United States Patent
Penner

(10) Patent No.: US 7,273,457 B2
(45) Date of Patent: Sep. 25, 2007

(54) BAROMETRIC PRESSURE CORRECTION BASED ON REMOTE SOURCES OF INFORMATION

(75) Inventor: Avi Penner, Tel Aviv (IL)

(73) Assignee: Remon Medical Technologies, Ltd., Caesarea (IL)

( * ) Notice: Subject to any disclaimer, the term of this patent is extended or adjusted under 35 U.S.C. 154(b) by 731 days.

(21) Appl. No.: 10/152,091

(22) Filed: May 20, 2002

(65) Prior Publication Data

US 2002/0177782 A1    Nov. 28, 2002

Related U.S. Application Data

(63) Continuation-in-part of application No. 09/989,912, filed on Nov. 19, 2001, now Pat. No. 7,024,248, which is a continuation-in-part of application No. 09/888,272, filed on Jun. 21, 2001, now Pat. No. 6,764,446, which is a continuation-in-part of application No. 09/690,615, filed on Oct. 16, 2000, now Pat. No. 6,628,989.

(51) Int. Cl.
    *A61B 5/00*    (2006.01)
(52) U.S. Cl. .................................... 600/561
(58) Field of Classification Search ................ 600/561, 600/509; 607/60, 32; 128/903, 904, 899; 340/601; 709/203, 228
    See application file for complete search history.

(56) References Cited

U.S. PATENT DOCUMENTS

| 4,651,740 A | 3/1987 | Schroeppel |
| 6,155,267 A * | 12/2000 | Nelson .................... 128/899 |
| 6,200,265 B1 | 3/2001 | Walsh et al. |
| 6,234,973 B1 | 5/2001 | Meador et al. ............. 600/486 |
| 6,236,889 B1 | 5/2001 | Soykan et al. |
| 6,248,080 B1 | 6/2001 | Miesel et al. .............. 600/561 |
| 6,738,671 B2 * | 5/2004 | Christophersom et al. .... 607/60 |
| 6,970,742 B2 | 11/2005 | Mann et al. |
| 2002/0023123 A1* | 2/2002 | Madison .................... 709/203 |
| 2002/0045921 A1 | 4/2002 | Wolinsky et al. |
| 2003/0169174 A1* | 9/2003 | Liebenow .................. 340/601 |

FOREIGN PATENT DOCUMENTS

| WO | WO99-34453 | 7/1999 |
| WO | WO 200058744 A1 * | 10/2000 |
| WO | WO 01-28627 A1 | 4/2001 |
| WO | WO 01-74278 A2 | 10/2001 |
| WO | WO 02/03347 A | 1/2002 |

OTHER PUBLICATIONS

PCT International Preliminary Examination Report for PCT/IB03/01741, Applicant: Remon Medical Technologies, LTD, Forms PCT/IPEA/ 409 and 416, dated Aug. 23, 2004 (9 pages).

* cited by examiner

*Primary Examiner*—Max F. Hindenburg
*Assistant Examiner*—Brian Szmal
(74) *Attorney, Agent, or Firm*—Vista IP Law Group LLP

(57) ABSTRACT

The invention includes systems and methods for converting absolute pressure data acquired in anatomical environments to gauge pressure data using an implant configured to monitor pressure. The implant is configured to communicate with an external controller, which is configured to communicate with a remote microprocessor that includes real-time barometric pressure data for one or more geographic locations.

32 Claims, 17 Drawing Sheets

BAROMETRIC PRESSURE CORRECTION BASED ON REMOTE SOURCES OF INFORMATION

RELATED APPLICATION DATA

This is a continuation-in-part of U.S. application Ser. No. 09/989,912, filed Nov. 19, 2001 now U.S. Pat. No. 7,024,248, which is a continuation-in-part of U.S. application Ser. No. 09/690,615, filed Oct. 16, 2000 now U.S. Pat. No 6,628,989. This is also a continuation-in-part of U.S. application Ser. No. 09/888,272, filed Jun. 21, 2001 now U.S. Pat. No. 6,764,446, which is a continuation-in-part of U.S. application Ser. No. 09/690,615, filed Oct. 16, 2000. The aforementioned applications are all incorporated herein by reference in their entireties.

FIELD OF THE INVENTION

The present invention relates generally to barometric pressure correction in implantable biosensors, and more particularly to barometric pressure correction for implantable pressure sensors based on remote sources of information, including remote databases and web sites.

BACKGROUND OF THE INVENTION

Devices are known that may be implanted within a patient's body for monitoring one or more physiological conditions and/or to provide therapeutic functions. For example, sensors or transducers may be located deep within the body for monitoring a variety of properties, such as temperature, pressure, strain, fluid flow, chemical properties, electrical properties, magnetic properties, and the like. In addition, devices may be implanted that perform one or more therapeutic functions, such as drug delivery, defibrillation, electrical stimulation, and the like.

Often it is desirable to communicate with such devices once they are implanted within a patient using an external controller, for example, to obtain data, and/or to activate or otherwise control the implant. An implant may include wire leads from the implant to an exterior surface of the patient, thereby allowing an external controller or other device to be directly coupled to the implant. Alternatively, the implant may be remotely controlled, e.g., using an external induction device. For example, an external radio frequency (RF) transmitter may be used to communicate with the implant. RF energy, however, may only penetrate a few millimeters into a body, because of the body's dielectric nature, and therefore may not be able to communicate effectively with an implant that is located deep within the body. In addition, although an RF transmitter may be able to induce a current within an implant, the implant's receiving antenna, generally a low impedance coil, may generate a voltage that is too low to provide a reliable switching mechanism.

In a further alternative, electromagnetic energy may be used to control an implant, since a body generally does not attenuate magnetic fields. The presence of external magnetic fields encountered by the patient during normal activity, however, may expose the patient to the risk of false positives, i.e., accidental activation or deactivation of the implant. Furthermore, external electromagnetic systems may be cumbersome and may not be able to effectively transfer coded information to an implant.

Notably, implantable biosensors that measure pressure deep within anatomical structures such as blood vessels or the brain, can only communicate the absolute pressure associated with the immediate anatomical environment. These devices are not capable of communicating gauge pressure because they are confined and sealed away from the ambient pressure external the body. In most cases, it is gauge pressure and not absolute pressure that is sought to be known, since the body regulates its activities based on the ambient pressure. Gauge pressure may be determined by correlating the absolute pressure with the ambient pressure. For example, Miesel et al. (U.S. Pat. No. 6,248,080), which isincorporated herein by reference, uses a barometer to determine gauge pressure based on a correlation of absolute pressure and ambient pressure. The Miesel system, however, requires a barometer to determine the ambient pressure.

SUMMARY OF THE INVENTION

The invention is generally directed to systems and methods for measuring pressure in a sealed or isolated system by converting or correcting data received from the sealed or otherwise isolated system using one or more remote databases. This generally involves a sensor placed within an isolated or enclosed system. Such enclosed systems can include anatomical structures such as blood vessels within a human circulatory system or other anatomical locations. They can also include isolated systems associated with automobiles, such as braking systems, cooling systems, cylinders and combustion chambers of an internal combustion engine, air intake systems, fuel systems including carburetors, electrical systems, air conditioning and heating systems, etc. The sensors can include those that are capable of measuring pressure, temperature, electrical impedance, position, strain, pH, fluid flow, chemical properties, electrical properties, magnetic properties and the like. An external monitor is used to communicate with the isolated sensor and obtain data about the parameters that are monitored by the sensor. The communication means can be wireless and can involve the transmission and reception of any type of telemetric signal including acoustic, RF, microwave, electromagnetic, light (e.g. infrared), etc. The external monitor can include one or more transducers to convert the telemetric signal into an electric signal, which can be processed by a microprocessor integrated into the external monitor. The external monitor can also include a GPS receiver to communicate geographic location data including altitude data to the microprocessor. The external monitor can communicate through various means known in the art with an external or remote database that includes real-time data, such as real-time temperature or barometric pressure data associated with numerous geographic locations. The remote database can be associated with a web site such as Yahoo® weather, weather.com, AWS.com, etc. The external monitor can use specific information obtained from the remote database to correct data received from the sensor. It can also use the real-time data to calibrate a measurement device, such as a barometer, which can be an integrated component of the external monitor or a stand-alone device in communication with the external monitor.

In one embodiment, the invention is directed to a system for measuring pressure in a body. The system includes an implant device configured for measuring absolute pressure in a body. The implant is also configured to communicate any measured absolute pressure information outside of the body using telemetric signals. The system also includes an external monitor that is configured to receive telemetric signals from the implant device. It is also configured to receive barometric pressure information from a remote source. The barometric pressure information can be associated with the geographic location of the body. The external monitor is also configured to derive gauge pressure from the received absolute pressure information and barometric pressure information. The remote source with which the external monitor is configured to communicate can be associated with a web site that includes weather information, such as barometric pressure information for numerous locations around the world. The system can also include a global position system (GPS) signal receiver, which can be coupled either to the implant device or to the external monitor. Thus, both or either the implant device or the external monitor can be configured to receive geographic position information from the GPS signal receiver. The external monitor can be configured to communicate this position information to the remote source, and to request and receive barometric pressure information that corresponds with the geographic position.

In another embodiment, the invention is directed to a method for measuring pressure in a body. The method includes receiving a telemetric signal from a biosensor implanted in a body. The telemetric signal can represent absolute pressure information or data. The method also includes receiving real-time barometric pressure information from a remote source, the real-time barometric pressure information corresponding to a geographic location of the body. The geographic location of the body can be determined in a number of ways including using a GPS receiver, a postal code, or a telephone number. Gauge pressure is then derived from the absolute pressure information and barometric pressure information, and can be displayed on a display proximate the body, such as on an external monitor or a computer monitor. The gauge pressure can be derived by the external monitor, the implanted biosensor, or the remote source. The remote source can, for example, be associated with a web site that includes weather information such as Yahoo® weather, Weather.com, AWS.com, or any other web site that provides barometric pressure data for numerous geographic locations. Alternatively, it can be a restricted proprietary database available only for the purpose of correcting absolute pressure data.

Other objects and features of the present invention will become apparent from consideration of the following description taken in conjunction with the accompanying drawings.

BRIEF DESCRIPTION OF THE DRAWINGS

The invention is herein described, by way of example only, with reference to the accompanying drawings, wherein.

DESCRIPTION OF THE PREFERRED EMBODIMENTS

Figure 1A:
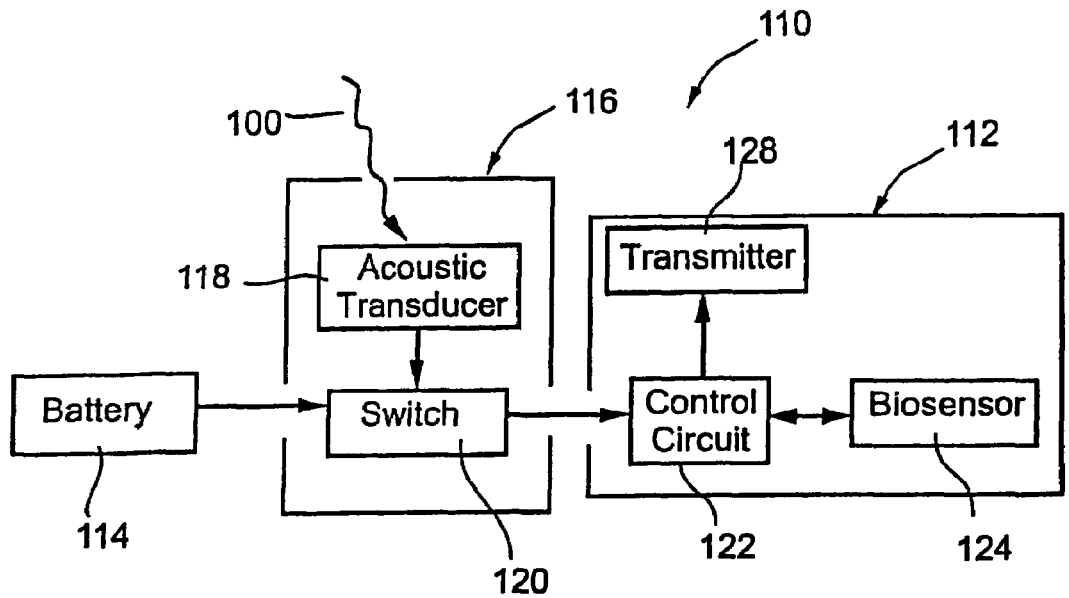
FIGS. 1A-1C are schematic drawings, showing exemplary embodiments of an implant, in accordance with the present invention.
Figure 1B:
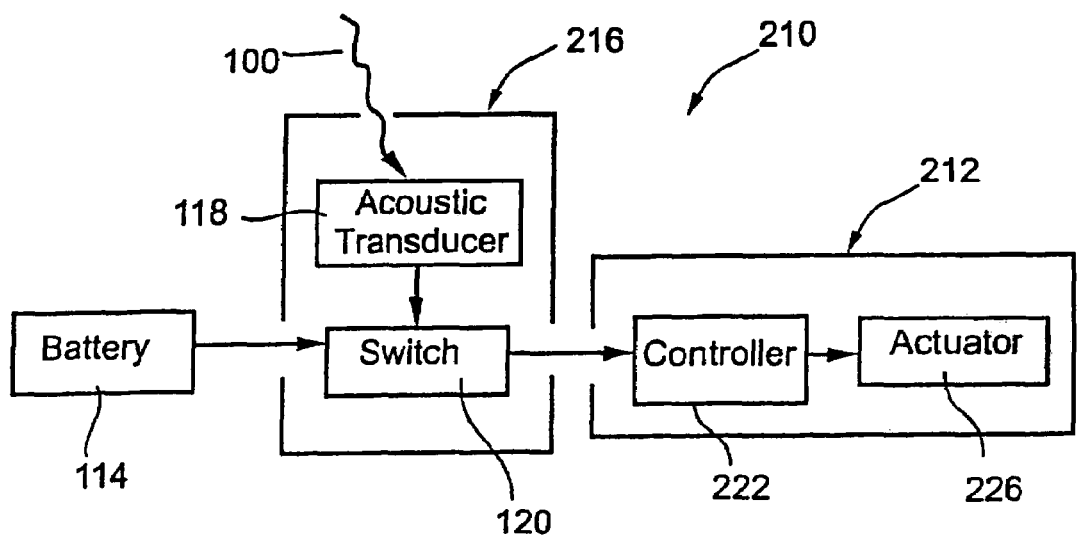
Figure 1C:
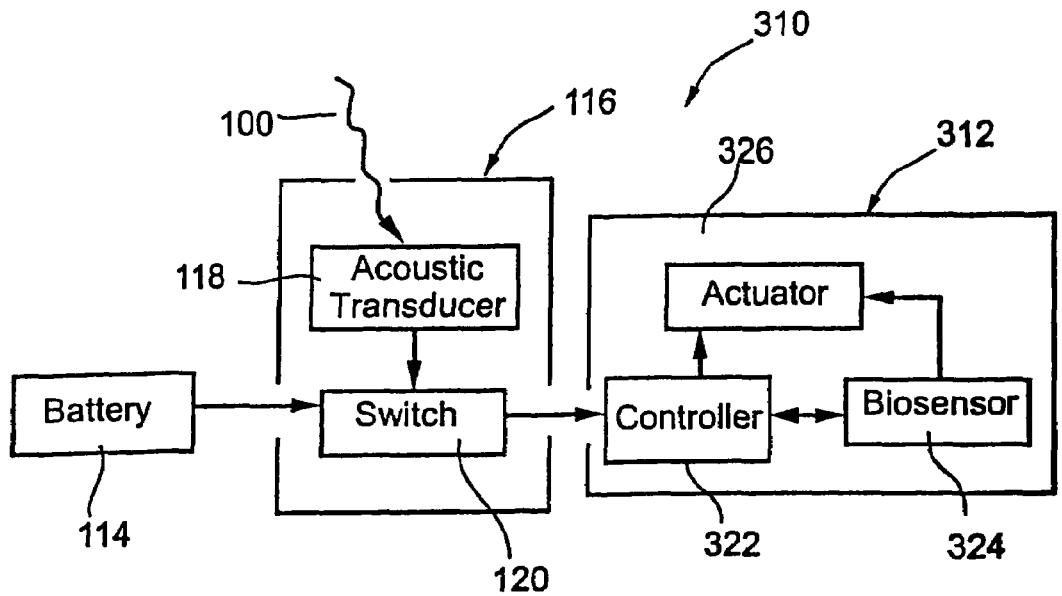

Turning to the drawings, various embodiments of biosensor implants and external controllers (also referred to as external monitors) configured to communicate with biosensor implants are first shown and described. FIGS. 1A-1C schematically show several exemplary embodiments of an implant 110, 210, 310, in accordance with the present invention. Generally, the implant 110, 210, 310 includes an electrical circuit 112, 212, 312 configured for performing one or more functions or commands when the implant 110, 210, 310 is activated, as described further below. In addition, the implant 110, 210, 310 includes an energy storage device 114 and optionally may include a switch 116 coupled to the electrical circuit 112, 212, 312 and the energy storage device 114. The switch 116 may be activated upon acoustic excitation 100 from an external acoustic energy source (not shown) to allow current flow from the energy storage device 114 to the electrical circuit 112, 212, 312.

In one embodiment, the switch 116 includes an acoustic transducer 118, such as that disclosed in PCT Publication No. WO 99/34,453, published Jul. 8, 1999, or in U.S. application Ser. No. 09/888,272, filed Jun. 21, 2001, the disclosures of which are expressly incorporated herein by reference. In addition, the switch 116 also includes a switch circuit 120, such as switch circuit 400 shown in FIG. 2, although alternatively other switches, such as a miniature electromechanical switch and the like (not shown) may be provided. In a further alternative, the acoustic transducer 118 may be coupled to the electrical circuit 112, 212, 312 and/or the energy storage device 114, and the switch circuit 120 may be eliminated.

The energy storage device 114 may be any of a variety of known devices, such as an energy exchanger, a battery and/or a capacitor (not shown). Preferably, the energy storage device 114 is capable of storing electrical energy substantially indefinitely for as long as the acoustic switch 116 remains open, i.e., when the implant 110, 210, 310 is in a "sleep" mode. In addition, the energy storage device 114 may be capable of being charged from an external source, e.g., inductively using acoustic telemetry, as will be appreciated by those skilled in the art. In an exemplary embodiment, the energy storage device 114 includes both a capacitor and a primary, non-rechargeable battery. Alternatively, the energy storage device 114 may include a secondary, rechargeable battery and/or capacitor that may be energized before activation or use of the implant 110, 210, 310.

The implant 110, 210, 310 may be surgically or minimally invasively inserted within a human body in order to carry out a variety of monitoring and/or therapeutic functions. For example, the electrical circuit 112, 212, 312 may include a control circuit 122, 222, 322, a biosensor 124, 224, an actuator 226, 326, and/or a transmitter 128, as explained in application Ser. No. 09/690,015, incorporated by reference above. The implant 210, 310 may be configured for providing one or more therapeutic functions, for example, to activate and/or control a therapeutic device implanted within a patient's body, such as an atrial defibrillator or pacemaker, a pain relief stimulator, a neuro-stimulator, a drug delivery device, and/or a light source used for photodynamic therapy. Alternatively, the implant may be used to monitor a radiation dose including ionizing, magnetic and/or acoustic radiation, to monitor flow in a bypass graft, to produce cell oxygenation and membrane electroporation, and the like. In addition or alternatively, the implant 110 may be used to measure one or more physiological parameters within the patient's body, such as pressure, temperature, electrical impedance, position, strain, pH, and the like.

The implant may operate in one of two modes, a "sleep" or "passive" mode when the implant remains dormant and not in use, i.e., when the acoustic switch 116 is open, and an "active" mode, when the acoustic switch 116 is closed, and electrical energy is delivered from the energy storage device 114 to the electrical circuit 112, 212, 312. Alternatively, the implant may operate continuously or intermittently. Because the acoustic switch 116 is open in the sleep mode, there is substantially no energy consumption from the energy storage device 114, and consequently, the implant may remain in the sleep mode virtually indefinitely, i.e., until activated. Thus, an implant in accordance with the present invention may be more energy efficient and, therefore, may require a relatively small energy storage device than implants that continuously draw at least a small amount of current in their "passive" mode.

Turning to FIG. 1A, an exemplary embodiment of an implant 110 is shown in which the electrical circuit 112 includes a control circuit 122, a biosensor 124 coupled to the controller 122, and a transmitter 128 coupled to the control circuit 122. The controller 122 may include circuitry for activating or controlling the biosensor 124, for receiving signals from the biosensor 124, and/or for processing the signals into data, for example, to be transmitted by the transmitter 128. Optionally, the electrical circuit 112 may include memory (not shown) for storing the data. The transmitter 128 may be any device capable of transmitting data from the control circuit 122 to a remote location outside the body, such as an acoustic transmitter, a radio frequency transmitter, and the like. Preferably, the control circuit 122 is coupled to the acoustic transducer 118 such that the acoustic transducer 118 may be used as a transmitter 128, as well as a receiver, instead of providing a separate transmitter.

The biosensor 124 may include one or more sensors capable of measuring physiological parameters, such as pressure, temperature, electrical impedance, position, strain, pH, fluid flow, electrochemical sensor, and the like. Thus, the biosensor 124 may generate a signal proportional to a physiological parameter that may be processed and/or relayed by the control circuit 122 to the transmitter 128, which, in turn, may generate a transmission signal to be received by a device outside the patient's body. Data regarding the physiological parameter(s) may be transmitted continuously or periodically until the acoustic switch 116 is deactivated, or for a fixed predetermined time, as will be appreciated by those skilled in the art.

Turning to FIG. 1B, another exemplary embodiment of an implant 210 is shown in which the electrical circuit 212 includes a control circuit 222 and an actuator 226. The actuator 226 may be coupled to a therapeutic device (not shown) provided in or otherwise coupled to the implant 210, such as a light source, a nerve stimulator, a defibrillator, an electrochemical oxidation/reduction electrode, or a valve communicating with an implanted drug reservoir (in the implant or otherwise implanted within the body in association with the implant).

When the switch 120 is closed, the control circuit 222 may activate the actuator 226 using a pre-programmed protocol, e.g., to complete a predetermined therapeutic procedure, whereupon the switch 120 may automatically open, or the controller 222 may follow a continuous or looped protocol until the switch 120 is deactivated. Alternatively, the acoustic transducer 118 may be coupled to the control circuit 222 for communicating a new or unique set of commands to the control circuit 222. For example, a particular course of treatment for a patient having the implant 210 may be determined, such as a flow rate and duration of drug delivery, drug activation, drug production, or an energy level and duration of electrical stimulation. Acoustic signals including commands specifying this course of treatment may be transmitted from an external controller (not shown), as described below, to the acoustic switch 116, e.g., along with or subsequent to the activation signal 100. The control circuit 222 may interpret these commands and control the actuator 226 accordingly to complete the course of treatment.

Turning to FIG. 1C, yet another exemplary embodiment of an implant 310 is shown in which the electrical circuit 312 includes a control circuit 322, a biosensor 324, and an actuator 326, all of which may be coupled to one another. This embodiment may operate similarly to the embodiments described above, e.g., to obtain data regarding one or more physiological parameters and/or to control a therapeutic device. In addition, once activated, the control circuit 322 may control the actuator 326 in response to data obtained from the biosensor 324 to control or adjust automatically a course of treatment being provided by a device connected to the actuator 326. For example, the actuator 326 may be coupled to an insulin pump (not shown), and the biosensor 324 may measure glucose levels within the patient's body. The control circuit 322 may control the actuator to open or close a valve on the insulin pump to adjust a rate of insulin delivery based upon glucose levels measured by the biosensor 324 in order to maintain the patient's glucose within a desired range.

Figure 2:
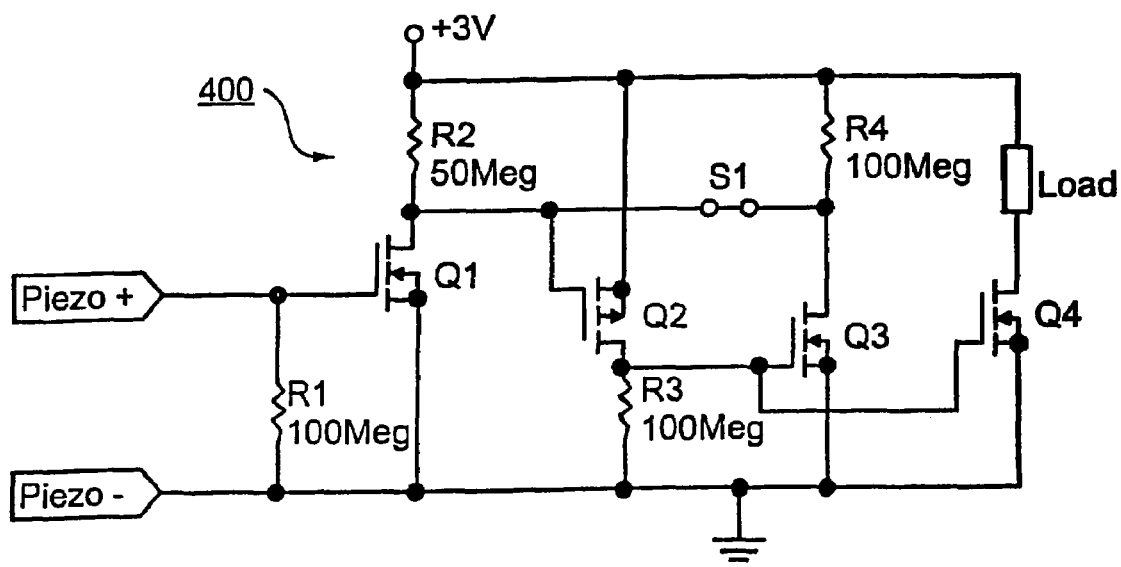
FIG. 2 is a schematic of an exemplary circuit for use as an acoustic switch, in accordance with the present invention.

Turning to FIG. 2, an exemplary embodiment of a switch 400 is shown that may be incorporated into an implant in accordance with the present invention. The switch 400 includes a piezoelectric transducer, or other acoustic transducer (not shown, but generally connected to the switch 400 at locations piezo + and piezo −), a plurality of MOSFET transistors (Q1-Q4) and resistors (R1-R4), and switch S1. A "load" may be coupled to the switch 400, such as one of the electrical circuits described above. In the switch's "sleep" mode, all of the MOSFET transistors (Q1-Q4) are in an off state. To maintain the off state, the gates of the transistors are biased by pull-up and pull-down resistors. The gates of N-channel transistors (Q1, Q3 & Q4) are biased to ground and the gate of P-channel transistor Q2 is biased to +3V. During this quiescent stage, switch S1 is closed and no current flows through the circuit. Therefore, although an energy storage device (not shown, but coupled between the hot post, labeled with an exemplary voltage of +3V, and ground) is connected to the switch 400, no current is being drawn therefrom since all of the transistors are quiescent.

When the acoustic transducer of the implant detects an external acoustic signal, e.g., having a particular frequency, such as the transducer's resonant frequency, the voltage on the transistor Q1 will exceed the transistor threshold voltage of about one half of a volt. Transistor Q1 is thereby switched on and current flows through transistor Q1 and pull-up resistor R2. As a result of the current flow through transistor Q1, the voltage on the drain of transistor Q1 and the gate of transistor Q2 drops from +3V substantially to zero (ground). This drop in voltage switches on the P-channel transistor Q2, which begins to conduct current through transistor Q2 and pull-down resistor R3.

As a result of the current flowing through transistor Q2, the voltage on the drain of transistor Q2 and the gates of transistors Q3 and Q4 increases from substantially zero to +3V. The increase in voltage switches on transistors Q3 and Q4. As a result, transistor Q3 begins to conduct current through resistor R4 and main switching transistor Q4 begins to conduct current through the "load," thereby switching on the electrical circuit.

As a result of the current flowing through transistor Q3, the gate of transistor Q2 is connected to ground through transistor Q3, irrespective of whether or not transistor Q1 is conducting. At this stage, the transistors (Q2, Q3 & Q4) are latched to the conducting state, even if the piezoelectric voltage on transistor Q1 is subsequently reduced to zero and transistor Q1 ceases to conduct. Thus, main switching transistor Q4 will remain on until switch S1 is opened.

In order to deactivate or open the switch 400, switch S1 must be opened, for example, while there is no acoustic excitation of the piezoelectric transducer. If this occurs, the gate of transistor Q2 increases to +3V due to pull-up resistor R2. Transistor Q2 then switches off, thereby, in turn, switching off transistors Q3 and Q4. At this stage, the switch 400 returns to its sleep mode, even if switch S1 is again closed. The switch 400 will only return to its active mode upon receiving a new acoustic activation signal from the piezoelectric transducer.

It should be apparent to one of ordinary skill in the art that the above-mentioned electrical circuit is not the only possible implementation of a switch for use with the present invention. For example, the switching operation my be performed using a CMOS circuit, which may draw less current when switched on, an electromechanical switch; and the like.

Figure 3:
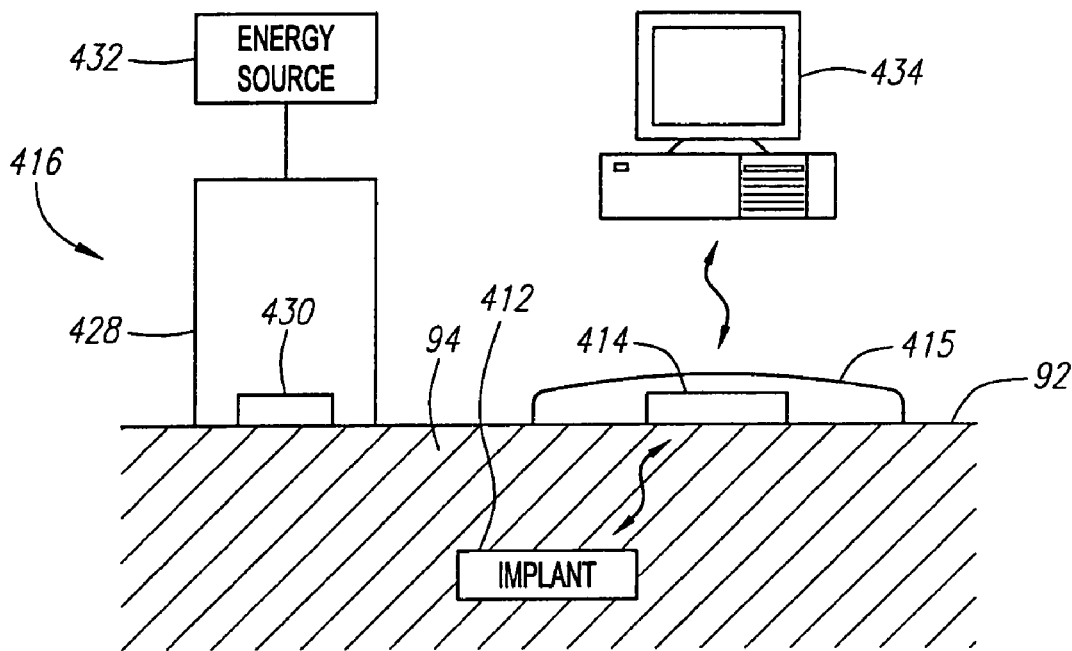
FIG. 3 is a cross-sectional view of a patient's body, showing a system for communicating with an implant, in accordance with the present invention.
Figure 4:
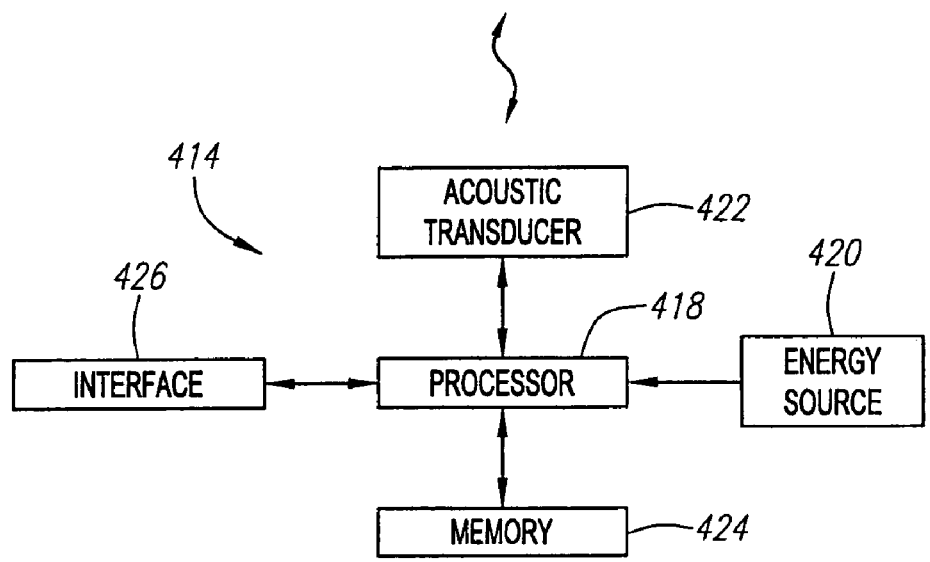
FIG. 4 is a schematic of an external monitor for communicating with an implant, such as that shown in FIG. 3, in accordance with the present invention.

Turning to FIGS. 3 and 4, a system 410 is shown for communicating with an implant 412, such as one of those described above. Generally, the system 410 includes an external communications device or controller 414, and may include a charger 416, one or more implants 412 (only one shown for simplicity), and an external recorder, computer, or other electronic device 434.

With particular reference to FIG. 4, the external controller 414 may include a processor or other electrical circuit 418 for controlling its operation, and an energy source 420, e.g., a nonrechargeable or a rechargeable battery, coupled to the processor 418 and/or other components of the controller 414, such as a power amplifier or an oscillator (not shown). In addition, the controller 414 may include one or more acoustic transducers 422 that are configured for converting between electrical energy and acoustic energy, similar to those described above. As shown, a single acoustic transducer 422 is provided that may communicate using acoustic telemetry, i.e., capable both of converting electrical energy to acoustic energy to transmit acoustic signals, and converting acoustic energy to electrical energy to receive acoustic signals, as explained further below. Alternatively, separate and/or multiple acoustic transducers may be provided for transmitting and receiving acoustic signals.

In one embodiment, the controller 414 also includes memory 424 coupled to the processor 418, e.g., for storing data provided to the controller 414, as explained further below. The memory 424 may be a temporary buffer that holds data before transfer to another device, or non-volatile memory capable of storing the data substantially indefinitely, e.g., until extracted by the processor 418 or other electronic device. For example, the memory 424 may be a memory card or an eprom (not shown) built into the controller 414 or otherwise coupled to the processor 418. The controller 414 may also include an interface 426, such as a lead or connector, or a transmitter and/or receiver, that may communicate with the external electronic device, as explained further below.

Preferably, the controller 414 is carried by a patch 415 that may be secured to a patient, e.g., to the patient's skin 92. For example, the patch 415 may include one or more layers of substantially flexible material to which the controller 414 and/or its individual components are attached. The patch 415 may include a single flexible membrane (not shown) to which the controller 414 is bonded or otherwise attached, e.g., using a substantially permanent adhesive, which may facilitate the patch 415 conforming to a patient's anatomy. Alternatively, the controller 414 may be secured between layers of material, e.g., within a pouch or other compartment (not shown) within the patch 415. For example, the patch 415 may include a pair of membranes (not shown) defining the pouch or compartment. The space within which the controller 414 is disposed may be filled with material to acoustically couple the acoustic transducer(s) (formed, for example, from PZT, composite PZT, Quartz, PVDF, and/or other piezoelectric material) of the controller 414 to an outer surface of the patch 415. Alternatively, the acoustic transducer(s) may be exposed, e.g., in a window formed in a wall of the patch 415.

The patch 415 may be formed from a flexible piezoelectric material, such as PVDF or a PVDF copolymer. Such polymers may allow the patch 415 to produce ultrasonic waves, as well as allowing the controller 414 to be secured to the patient's skin 92. Thus, the wall of the patch 415 itself may provide an acoustic transducer for the controller 414, i.e., for transmitting acoustic energy to and/or receiving acoustic energy from the implant 412.

The patch 415 may then be secured to the patient's skin 92 using a material, such as a layer of adhesive (not shown), substantially permanently affixed or otherwise provided on a surface of the patch. The adhesive may be hydrogel, silicon, polyurethane, polyethylene, polypropylene, fluorocarbon polymer, and the like. Alternatively, a separate adhesive may be applied to the patch 415 and/or to the patient's skin 92 before applying the patch 415 in order to secure the controller 414 to the patient's skin 92. Such an adhesive may enhance acoustically coupling of the acoustic transducer(s) of the controller 414 to the patient's skin 92, and consequently to the implant 412 within the patient's body 94. Optionally, additional wetting material, including water, silicone oil, silicone gel, hydrogel, and the like, and/or other acoustically conductive material may be provided between the patch 415 or the acoustic transducer 422, and the patient's skin 92, e.g., to provide substantial continuity and minimize reflection or other losses and/or to secure the patch 415 to the patient.

Alternatively, the controller 414 may be carried by a belt (not shown) that may be secured around the patient, e.g., such that the acoustic transducer 422 is secured against the patient's skin. The belt may carry other components of the system 410, e.g., an external power supply for the controller 414. For example, a battery pack (not shown) may be carried by the belt that may be coupled to the controller 414 for providing electrical energy for its operation.

The patch 415 may be relatively light and compact, for example, having a maximum surface dimension (e.g., width or height) not more than about ten to two hundred millimeters (10-200 mm), a thickness not more than about five to one hundred millimeters (5100 mm), and a weight not more than about twenty to four hundred grams (20-400 g), such that the controller 414 may be inconspicuously attached to the patient. Thus, the patient may be able to resume normal physical activity, without substantial impairment from the controller. Yet, the internal energy source of the controller 414 may be sufficiently large to communicate with the implant 412 for an extended period of time, e.g., for hours or days, without requiring recharging or continuous coupling to a separate energy source.

The system 410 may be used to control, energize, and/or otherwise communicate with the implant 412. For example, the controller 414 may be used to activate the implant 412. One or more external acoustic energy waves or signals 430 may be transmitted from the controller 414 into the patient's body 94, e.g., generally towards the location of the implant 412 until the signal is received by the acoustic transducer (not shown in FIGS. 3 and 4) of the implant 412. Upon excitation by the acoustic wave(s) 430, the acoustic transducer produces an electrical output that is used to close, open, or otherwise activate the switch (also not shown in FIGS. 3 and 4) of the implant 412. Preferably, in order to achieve reliable switching, the acoustic transducer of the implant 412 is configured to generate a voltage of at least several tenths of a volt upon excitation that may be used as an activation signal to close the switch, as described above.

As a safety measure against false positives (e.g., erroneous activation or deactivation), the controller 414 may be configured to direct its acoustic transducer 422 to transmit an initiation signal followed by a confirmation signal. When the acoustic transducer of the implant 412 receives these signals, the electrical circuit may monitor the signals for a proper sequence of signals, thereby ensuring that the acoustic switch of the implant 412 only closes upon receiving the proper initiation and confirmation signals. For example, the acoustic switch may only acknowledge an activation signal that includes a first pulse followed by a second pulse separated by a predetermined delay. Use of a confirmation signal may be particularly important for certain applications, for example, to prevent unintentional release of drugs by a drug delivery implant.

In addition to an activation signal, the controller 414 may transmit a second acoustic signal that may be the same as or different than the acoustic wave(s) used to activate the acoustic switch of the implant 412. Thus, the switch may be opened when the acoustic transducer of the implant 412 receives this second acoustic signal, e.g., by the acoustic transducer generating a termination signal in response to the second acoustic signal, in order to return the implant 412 to its sleep mode.

For example, once activated, the switch may remain closed indefinitely, e.g., until the energy storage device (not shown in FIGS. 3 and 4) of the implant 412 is completely depleted, falls below a predetermined threshold, or until a termination signal is received by the acoustic transducer of the implant 412 from the controller 414. Alternatively, the acoustic switch of the implant 412 may include a timer (not shown), such that the switch remains closed only for a predetermined time, whereupon the switch may automatically open, returning the implant 412 to its sleep mode.

Figure 5:
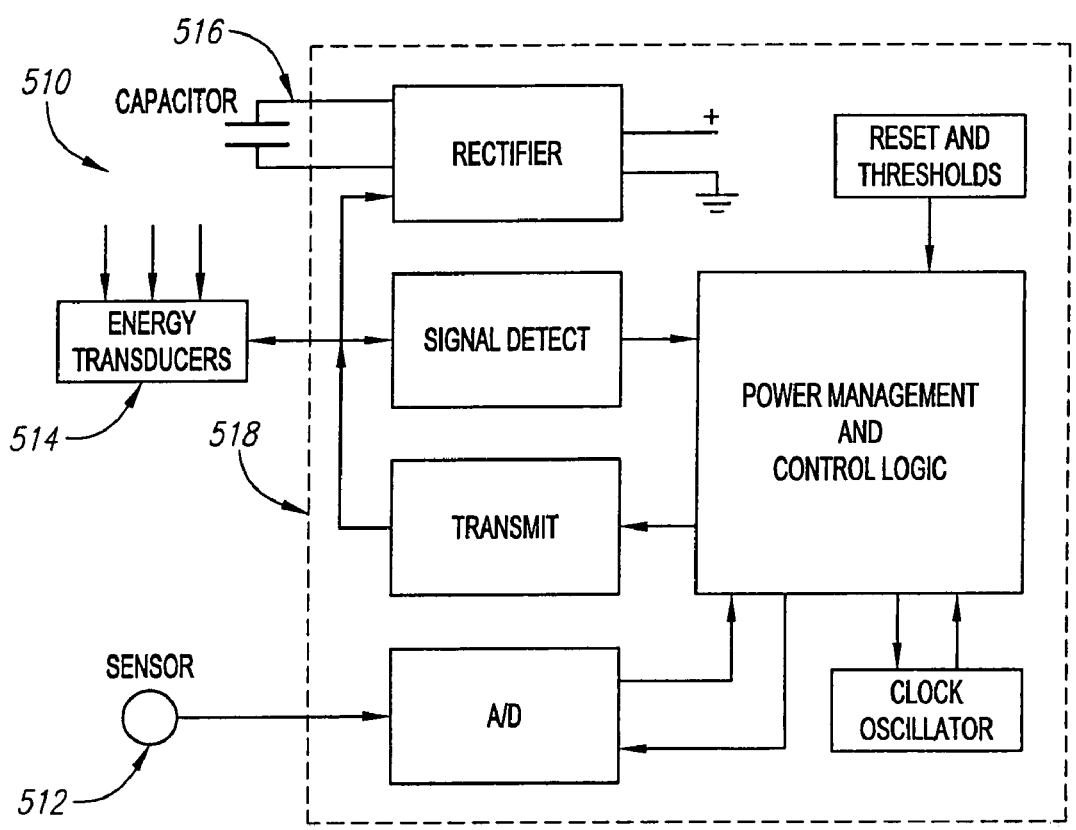
FIG. 5 is a schematic of another exemplary embodiment of an implant, in accordance with the present invention.

FIG. 5 shows an alternative embodiment of an implant 510 that does not include an acoustic switch. Generally, the implant includes a sensor 512, one or more energy transducers 514, one or more energy storage devices 516, and a control circuit 518, similar to the embodiments described above. The sensor 512 is preferably a pressure sensor for measuring intra-body pressure, such as an absolute variable capacitance type pressure sensor. In alternative embodiments, one or more other sensors may be provided instead of or in addition to a pressure sensor 512. For example, the sensor 512 may include one or more biosensors capable of measuring physiological parameters, such as temperature, electrical impedance, position, strain, pH, fluid flow, and the like. An external controller (not shown), such as that described above, may also be used to communicate with this implant.

Returning to FIG. 3, an external controller 414 in accordance with the present invention preferably has only sufficient power to control its own operation and to communicate with the implant 412. Because of its limited energy requirements, the controller 414 may be relatively small and portable, e.g., may be attached to the patient, while still allowing the patient to engage in normal physical activity. The controller 414 may be used to communicate with the implant 412, e.g., periodically activating or deactivating the implant 412, and/or recording data generated and transmitted by the implant 412. Because it is located outside the patient's body, the controller 414 may be more easily programmed or reprogrammed than the implant 412 itself, and/or may be repaired or replaced if necessary or desired.

In addition to the external controller 414, the system 410 may include one or more electronic devices 434 that may be coupled to the controller 414 via the interface 426, such as a recorder, a computer, a personal digital assistant, and/or a wireless device, such as a cellular telephone. The electronic device 434 may be directly coupled to the controller 414, by a connector or lead (not shown) extending from the patch 415 within which the controller 414 is provided. Alternatively, the controller 414 and/or patch 415 may include a wireless transmitter and/or receiver (not shown), e.g., a short-range RF transceiver, for communicating with the electronic device 434.

The electronic device 434 may be used to extract data from the memory 424 of the controller 414, e.g., sensor data and the like, received from the implant 412. This data may be included in a patient database maintained by health care professionals monitoring the patient receiving the implant 412. In addition, the electronic device 434 may be used to program the controller 414, e.g., to program commands, timing sequences, and the like.

The system 410 may also include an external charger 418. For example, the implant 412 may include a rechargeable energy storage device (not shown in FIG. 3), preferably one or more capacitors, that are coupled to the acoustic transducer (also not shown in FIG. 3). The charger 416 may include a probe 428, including an acoustic transducer 430 for contacting a patient's skin 92. The charger 416 also includes a source of electrical energy 432, such as a radio frequency (RF) generator, that is coupled to the acoustic transducer 430. The charger 418 may also include electrical circuits for controlling its operation and buttons or other controls (not shown) for activating and/or deactivating the acoustic transducer 430.

The charger 418 may be used to charge or recharge the implant, e.g., periodically or before each activation. Because the charger 418 includes a substantially more powerful energy source than the controller 414, the charger 418 is generally a relatively bulky device compared to the controller 414, in particular due to the energy generator, which may be stationary or of limited mobility. In addition, the charger 418 may be used to recharge the controller 414 periodically, e.g., by a direct or wireless coupling. Alternatively, the controller 414 and patch 415 may be disposable, e.g., after its energy has been depleted, and replaced with another.

For purposes of comparison, an exemplary charger 416 may need to generate about ten kiloPascals (10 kPa) of acoustic energy for about twenty seconds (20 sec.) in order to fully charge the implant 412. In contrast, an exemplary controller 414 may be limited to outputting relatively smaller bursts of acoustic energy for communicating with, but not charging, the implant 412. Such acoustic signals may have a duration of as little as about one millisecond (1 ms), as opposed to the significantly longer charging signals generated by the charger 416.

The transducer 422 of the controller 414 may consume about one Watt (1 W) of power to produce a 1 kPa acoustic signal for about one millisecond. If the controller 414 communicates with the implant 412 on an hourly basis, the energy source 420 of the controller 418 may only need sufficient capacity to provide 0.024 Watt seconds per day (0.024 W.sec./day). Because of this low energy requirement, the energy source 420, and, consequently, the controller 418, may be relatively compact and portable, as compared to the charger 416. Thus, the energy source 420 may be self-contained within the controller 418, i.e., carried by the patch 415. Alternatively, a portable energy source, e.g., an external battery pack (not shown) may be provided for supplying electrical energy to the controller 418 that may be carried by the patient, e.g., on a belt (not shown).

In an alternative embodiment, the controller and charger may be provided as a single device (not shown), e.g., including one or more acoustic transducers and/or one or more processors for performing the functions of both devices, as described above. In this embodiment, the implant 412 may operate in a "half-duplex" mode, a quasi-continuous mode, or in a "full-duplex" mode, as described in the applications incorporated above.

Figure 6:
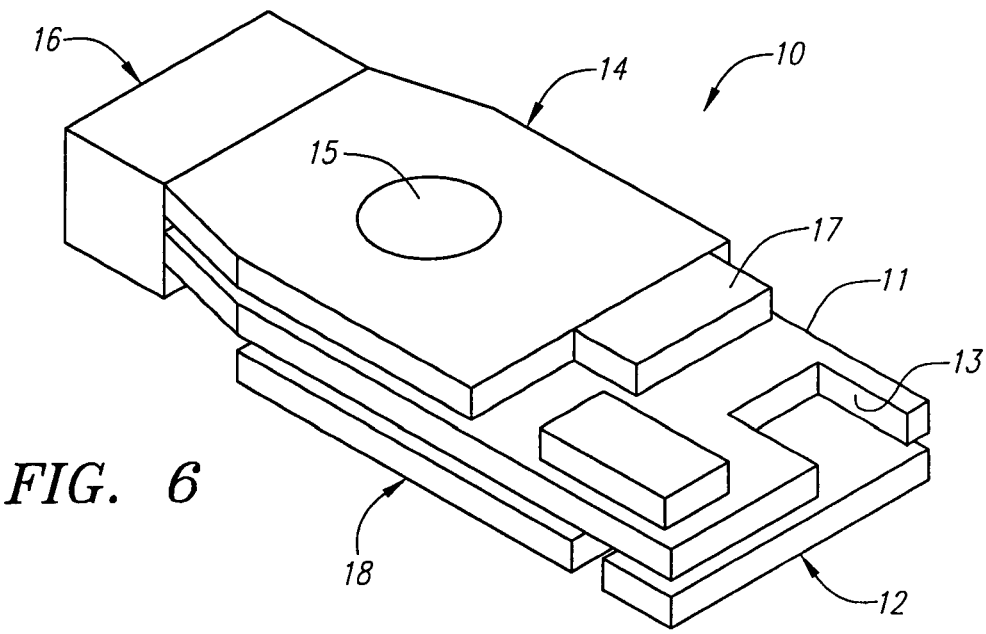
FIG. 6 is a perspective view of an exemplary embodiment of a pressure sensing implant, in accordance with the present invention.
Figure 7:
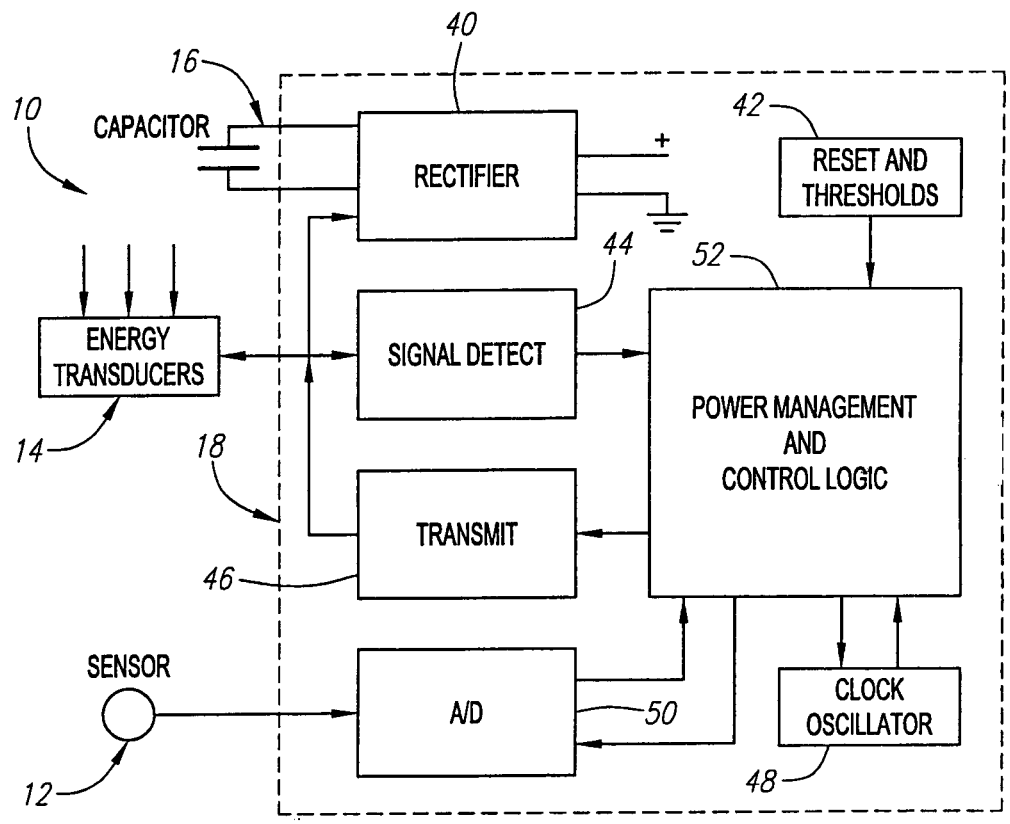
FIG. 7 is a schematic layout of the implant of FIG. 6.

FIGS. 6 and 7 show another embodiment of an implant 10, in accordance with the present invention. Generally, the implant 10 includes a sensor 12, one or more energy transducers 14, one or more energy storage devices 16, and a controller 18.

The sensor 12 is preferably a pressure sensor for measuring intra-body pressure. The sensor 12 may measure pressure within a range as low as a few millibars gauge (e.g., pressure ranges experienced within the cranium or within the pulmonary artery) and up to about 400 millibars gauge (e.g., blood pressure ranges experienced during systole). In addition, because the barometric pressure may vary by location, i.e., altitude, the absolute pressure range capacity of the sensor is preferably between about 650 and 1450 millibars absolute.

The sensor 12 can be an absolute variable capacitance type pressure sensor. Alternatively, a piezoresistive pressure sensor may be used, although the energy consumption of this type of sensor may be substantially higher than a variable capacitance pressure sensor. For example, a typical piezoresistive sensor may have a bridge resistance of about five kiloohms (5 kΩ). Assuming that one volt (1 V) is sufficient to allow pressure sampling, a current of at least about 0.2 milliAmperes (mA) would be required to operate the sensor. This may be about one hundred times more than the current required to obtain pressure samples using a variable capacitance pressure sensor.

Some reduction in power consumption of piezoresistive pressure sensors may be obtained by reducing the sampling rate of the sensor or otherwise reducing the duty cycle of the implant. Alternatively, to reduce power consumption, a sample-and-hold circuit (not shown) may be provided for capturing voltages, and an analog-to-digital converter (also not shown) may be provided for converting the voltages when desired. Thus, the current may be on for relatively short times during each sampling cycle.

Preferably, a silicon MEMS-based pressure sensor is used, because of its relative small size, e.g., smaller than about four millimeters (4 mm) maximum footprint, e.g., not more than about four millimeters (4 mm) width by four millimeters (4 mm) length. Preferably, the sensor is no larger than about 0.8 mm width by about 2.1 mm length by about 0.3 mm thickness. Silicon is a particularly useful material for the sensor 12, as it generally does not suffer from creep and fatigue, and therefore may result in a substantially stable sensor. MEMS-based sensors are presently preferred because they may be manufactured in large volume at relatively low cost compared to other sensors. Other materials that may be used include titanium, as is used for the Chronicle™ device manufactured by Medtronic, Inc. Preferably, the sensor 12 is made from biocompatible materials, although the sensor 12 may be coated, if necessary or desired, with a biocompatible and/or chemically resistive coating (not shown), as will be appreciated by those skilled in the art.

In alternative embodiments, one or more other sensors may be provided instead of or in addition to a pressure sensor. For example, the sensor 12 may include one or more biosensors capable of measuring physiological parameters, such as temperature, electrical impedance, position, strain, pH, fluid flow, and the like. U.S. Pat. No. 4,793,825 issued to Benjamin et al. and U.S. Pat. No. 5,833,603 issued to Kovacs et al. disclose additional exemplary embodiments of biosensors that may be provided. The disclosure of these references and others cited therein are expressly incorporated herein by reference. The sensor 12 may generate a signal proportional to a physiological parameter that may be processed and/or relayed by the controller 18 to the energy transducer 14, as described further below. Alternatively, the sensor 12 may be configured to monitor a radiation dose including ionizing, magnetic and/or acoustic radiation, to monitor flow in a bypass graft, to produce cell oxygenation and membrane electroporation, and the like.

In further alternatives, a device for providing one or more therapeutic functions (not shown) may be provided in addition to or instead of the sensor 12. For example, the device may be used to activate and/or control a therapeutic device implanted within a patient's body, such as an atrial defibrillator, a pain relief stimulator, a neuro-stimulator, a drug delivery device, and/or a light source used for photodynamic therapy.

Figure 8A:
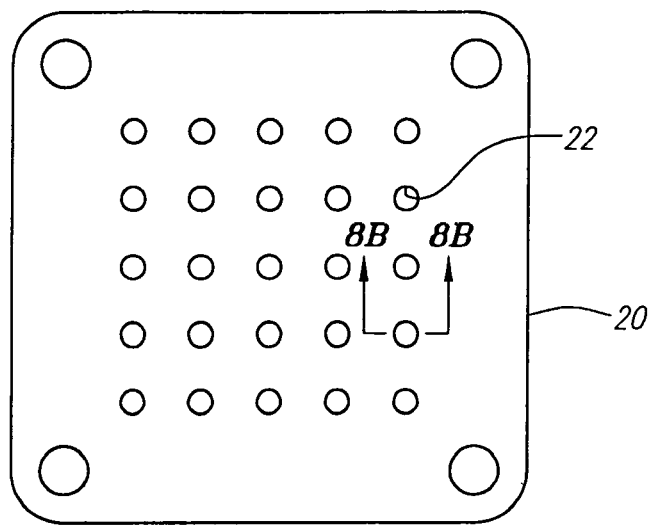
FIG. 8A is a top view of an energy exchanger that may be provided in an implant, such as that shown in FIGS. 6 and 7, in accordance with the present invention.
Figure 8B:
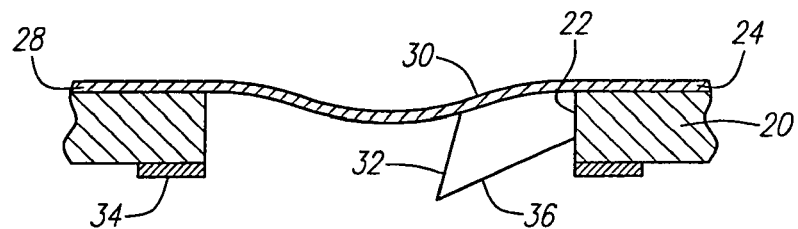
FIG. 8B is a cross-sectional view of the energy exchanger of FIG. 8A, taken along line B-B.

Turning to FIGS. 8A and 8B, the energy transducer 14 is preferably an acoustic transducer for converting energy between electrical energy and acoustic energy. As explained further below, the acoustic transducer 14 is configured for converting acoustic energy from a source external to the implant into electrical energy and/or for transmitting an acoustic signal including sensor data to a location external to the implant. In one embodiment, the energy transducer 14 is configured to operate alternatively as either an energy exchanger or an acoustic transmitter, or simultaneously as an energy exchanger and an acoustic transmitter. Alternatively, multiple energy transducers (not shown) may be provided, e.g., one or more converting acoustic energy striking the energy exchanger into electrical energy, and one or more transmitting acoustic signals to a location external to the implant 10. In a further alternative, multiple energy transducers (not shown) may be provided for increasing the electrical energy produced for a given acoustic energy transmitted to the implant 10.

The energy transducer 14 generally includes a substrate 20 including one or more cavities 22 therein, such as the array of cavities 22 shown in FIG. 8A. The cavities 22 may extend completely through the substrate 20 or only partially into the substrate 20. The cavities 22 are preferably substantially round in cross-section, although oval or other elongate slotted cavities (not shown) may be provided, which may increase sensitivity and/or efficiency as compared to a substantially round cavity. The cavities 22 may have a cross-section of about 0.52.5 millimeters, and preferably between about 1.0 and 1.3 millimeters (mm). For elliptical or other elongate cavities (not shown), the cavities preferably have a width of 0.2-2.5 millimeters and a length of 1.0-25 millimeters. The substrate 20 may be formed from a relatively high modulus polymer, such as poly ether ether ketone (PEEK), silicon, and/or a printed circuit board, e.g., of FR4, Rogers, a ceramic, or Kapton.

A substantially flexible piezoelectric layer 24 is attached to the substrate 20 across cavities 22. The piezoelectric layer 24 generally includes a polymer layer 28, preferably a fluorocarbon polymer, such as poly vinylidene fluoride (PVDF). The polymer layer 28 may have a thickness of between about three and two hundred fifty micrometers (3-250 μm), and preferably about thirty micrometers (30 μm) or less. A first conductive layer 30 is provided on an external surface of the polymer membrane 28 and a second conductive layer 32 provided on an internal surface of the polymer membrane 28. The second conductive layer 32 may be coupled to a conductive region 36 provided on a wall of the cavities 22. A pad 34 is provided on a lower surface of the substrate 20 for coupling the second conductive layer 32 to a printed circuit board (not shown), as described further below.

To manufacture the energy transducer 14, a substantially flexible polymer layer 28, such as a PVDF membrane, is provided. Because PVDF is generally chemically inert, the polymer layer 28 may need to be activated, e.g., using an etching process. For example, a sodium napthalene solution may be used to chemically attack the PVDF to cleave the carbonfluorine bonds and/or other solutions to cleave the carbon-hydrogen bonds and/or carbon-carbon bonds in the material. Alternatively, a gas phase plasma treatment, e.g., using an oxygen, air, Helium, and/or Argon plasma, may be used.

A substantially planar substrate 20 is provided, and one or more cavities 22 are formed in a surface of the substrate 20, for example, by mechanical drilling, laser drilling, or punching. Alternatively, the cavities 22 may be etched into the substrate 20, e.g., using VLSI/micro-machining technology or any other suitable technology.

A thin layer of adhesive (not shown) may be applied over the substrate 20, such as an epoxy or acrylic-based adhesive. Preferably, a relatively low viscosity (e.g., less than one thousand centi-poise) adhesive is used that may be atomized over the substrate 20. More preferably, the adhesive is light-activated, thereby facilitating positioning of the piezoelectric layer 24 over the substrate 20 before the adhesive is cured. The piezoelectric layer 24 is applied against the adhesive over the substrate 20. Alternatively, individual piezoelectric layers (not shown) may be bonded or otherwise attached over one or more individual cavities 22. The cavities 22 may be filled with a gas, such as air, to a predetermined pressure, e.g., ambient pressure or a predetermined vacuum, that may be selected to provide a desired sensitivity and ruggedness for the energy transducer 14.

The assembled substrate 20 and piezoelectric layer 24 may be placed in a pressure chamber, and a predetermined pressure applied against the piezoelectric layer 24. This may cause the piezoelectric layer 24 to press against the substrate 20, e.g., to facilitate spreading the adhesive more evenly between the substrate 20 and the piezoelectric layer 24. In addition, the predetermined pressure preferably causes the piezoelectric layer 24 to at least partially enter the cavities 22, thereby creating depressions in the piezoelectric layer 24 corresponding to the cavities 22, as best seen in FIG. 8B. Optionally, the pressure chamber may be heated to a predetermined temperature to facilitate creating the depressions and/or cure the adhesive. In addition or alternatively, the adhesive may then be cured, e.g., by exposing the assembled substrate 20 and piezoelectric layer 24 to visible or ultraviolet light, pressure, and/or heat for a predetermined time.

Thus, the piezoelectric layer 24 may include depressions, which may be useful for enhancing the efficiency and/or sensitivity of the energy transducer 12. For example, the depressions may enhance the conversion of an acoustic pressure wave striking the piezoelectric layer 24 into mechanical strain, resulting in an increased yield of electrical energy for a given pressure amplitude. The depressions may also be used to customize the natural resonant frequency of the piezoelectric layer 24. The depth of the depressions may be between about one and two hundred micrometers (1-200 µm), and preferably between about twenty and one hundred micrometers (20-100 µm), although depths greater than this may also increase efficiency as compared to a planar piezoelectric layer 24 without depressions. To ensure that these depths are consistently reproducible, the depth of the depressions may be measured, for example, using a non-contact optical profiler.

Both surfaces of the polymer layer 28 may be coated with conductive layers 30, 32, preferably metallization layers, at any stage of manufacturing. For example, the conductive layers 30, 32 may be applied either before or after the piezoelectric layer 24 has been bonded to the substrate 20. Because the current encountered during use of the energy transducer 14 is relatively low (e.g., about thirty microamperes (30 µA) or less, and preferably about five microamperes (5 µA) or less), a thickness of the conductive layers 30, 32 may be relatively thin, e.g., fifteen micrometers (15 µm) or less, and more preferably about two hundred nanometers (200 nm) or less. The thickness of the conductive layers 30, 32 may be substantially equal to or different from one another. For example, the first or outer conductive layer 30 may be substantially thicker than the second or inner conductive layer 32 to protect the energy transducer 14 from environments to which it is exposed, such as those encountered within a human body. The conductive layers 30, 32 may be formed from biocompatible and/or metallic materials, including one or more of gold, platinum, titanium, tantalum, palladium, vanadium, copper, nickel, silver, and the like.

The conductive layers 30, 32 may be coated on the surfaces of the polymer layer 28 using any known method, such as depositing an electro-less nickel, gold, or copper base layer, followed by depositing a galvanic coating, including any of the materials listed above. The conductive layers 30, 32 may be deposited using physical vapor deposition, chemical vapor deposition, sputtering, and/or other gas phase coating processes known to those skilled in the art. The conductive layers 30, 32 may be applied as single layers or as multiple layers of one or more materials in order to optimize the layers' electrical, mechanical, and/or chemical properties. Exemplary methods for making the piezoelectric layer 24 may be found in "Handbook of Physical Vapor Deposition (PVD) Processing," Donald M. Mattox (ISBN 0-8155-1422-0 Noyes publications, 1998) and "Handbook of Deposition Technologies for Films and Coatings," Rointan F. Bunshah (ed.), (Noyes Publications; ISBN: 0815513372 2nd edition 1994.) The disclosures of these references, as well as any others cited therein, are incorporated herein by reference.

The method described above may be used to make individual energy transducers or alternatively to make a plurality of energy transducers. For example, a plurality of energy transducers may be made as a single panel, and, after the metallization process, the panel may be separated into individual energy transducers. The separation may be accomplished using known dicing systems and methods, for example, using a dicing machine known to those in the microelectronics industry for dicing silicon wafers, a knife cutter, a milling machine, or a laser, e.g., a diode laser, a neodymium YAG laser, a $CO_2$ laser, or an excimer laser. Upon separation of the individual energy transducers, the electrical impedance of each of the energy transducers may be measured to confirm their integrity and proper operation. Additional information on acoustic transducers or energy exchangers appropriate for use with implants in accordance with the present invention may be found in U.S. Pat. No. 6,140,740, the disclosure of which is expressly incorporated herein by reference.

In an alternative embodiment, the substrate 20 may be formed from silicon, with or without electronics. The cavities 22 may be formed therein, the piezoelectric layer 24 may be attached to the substrate 20, and the surfaces metalized, generally as described above. In order to avoid large capacitances, an insulating oxide or other ring (not shown) may be provided around the cavities 22. The bottom of the cavities 22 may be sealed using an adhesive, e.g., an underfill adhesive used during the flip-chip process.

Returning to FIGS. 6 and 7, the energy storage device 16, preferably one or more capacitors, is coupled to the energy transducer 14. In an exemplary embodiment, the capacitor may be a tantalum or ceramic capacitor, e.g., a 10.0 µF. tantalum capacitor, such as model no. TACL106K006R, sold by AVX. Alternatively, the energy storage device 16 may be a battery or other known device, preferably capable of storing electrical energy substantially indefinitely. In addition, the energy storage device 16 may be capable of being charged from an external source, e.g., using acoustic energy, as described further below. In an alternative embodiment, the energy storage device 16 may include both a capacitor and a primary, non-rechargeable battery (not shown). Alternatively, the energy storage device 16 may include a secondary, rechargeable battery and/or capacitor that may be energized before activation or use of the implant 10. For example, the energy storage device 16 may include a first relatively fast-charging capacitor and a second relatively slow-charging capacitor (not shown).

Turning to FIG. 7, the controller 18 may be an Application Specific Integrated Circuit (ASIC) and/or a plurality of discrete electronic components. The controller 18 generally interfaces between the sensor 12, the energy transducer 14, and/or other active or passive components of the implant 10. The controller 18 is also coupled to the energy storage device 16 for receiving electrical energy to operate the controller 18 and/or other components of the implant 10. The controller 18 generally includes a rectifier 40, reset and threshold circuitry 42, signal detect circuitry 44, transmission circuitry 46, a clock oscillator 48, an analog-to-digital converter 50, and power management and control logic circuitry 52. In addition, the controller 18 may include a voltage reference circuit, e.g., a bandgap reference, a Zener device, or a buried Zener device.

The rectifier 40 is coupled to the energy transducer 14 for converting electrical. energy generated by the energy transducer 14 into a form suitable for powering components of the implant 10. For example, the rectifier 40 may be configured for converting incoming alternating current (AC) voltage from the energy transducer 14 into direct current (DC) voltage for storage by the energy storage device 16 and/or for powering the controller 18 and other components of the implant 10. The rectification may be performed by diodes arranged in a configuration suitable for the requirements of the mode of operation, preferably resulting in a passive circuit that draws substantially no current.

Figure 9:
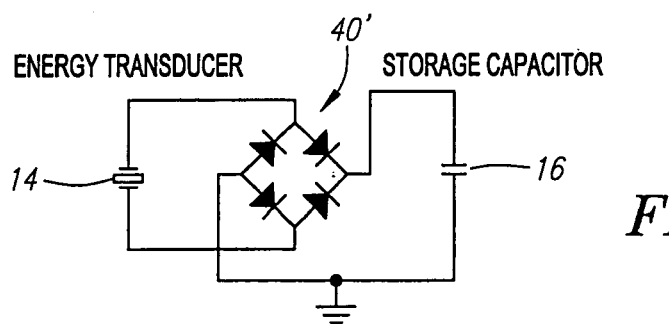
FIG. 9 is a schematic of an exemplary embodiment of a rectifier for use with an implant, such as that shown in FIG. 7.

FIG. 9 shows a first embodiment of a full-bridge rectifier 40' that may be provided. The energy transducer 14 and energy storage device 16 may be connected to the rectifier 40' such that AC current generated by the energy transducer 14 is converted into DC current for charging the energy storage device 16. The full-bridge configuration of the rectifier 40' may yield relatively high current and power efficiency that may be suitable for "full-duplex" operation of the energy transducer 14, i.e., where the energy transducer 14 simultaneously converts external acoustic energy into electrical energy and transmits an acoustic signal.

Figure 10:
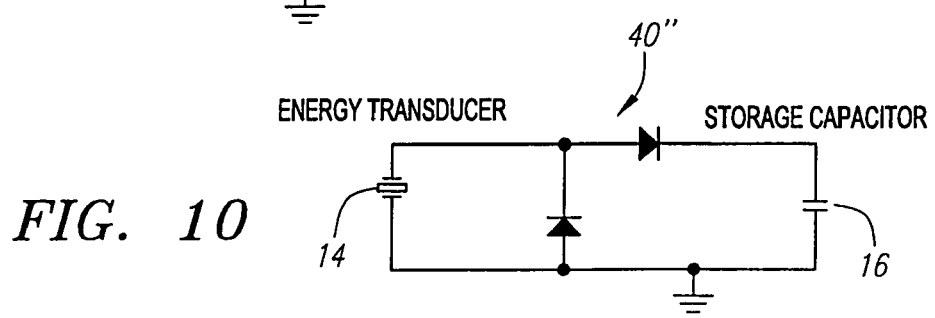
FIG. 10 is a schematic of another exemplary embodiment of a rectifier for use with an implant, such as that shown in FIG. 7.

FIG. 10 shows a second embodiment of a voltage-doubler rectifier 40" that may be used. The configuration of this rectifier 40" may yield less current than the rectifier 40' shown in FIG. 9, although it may generate a relatively higher voltage for a given acoustic excitation of the energy transducer 14. This rectifier 40" may be better suited for "half-duplex" operation, i.e., where the energizing and transmitting functions of the energy transducer 14 are temporally distinct. This embodiment may also only require two diodes to operate and may keep one side of the energy transducer 14 substantially grounded, thereby simplifying construction of the implant 10.

Alternatively, other rectification circuits (not shown) may be used, including Schottky diodes, voltage triplers or other multiplier circuits, and the like. In addition, the rectifier 40 may include an overvoltage protector (not shown), which may prevent the energy storage device 16 from overcharging, e.g., to unsafe levels. For example, the overvoltage protector may include a Zener diode, or a transistor that opens at a predetermined threshold voltage.

Returning to FIG. 7, the reset and threshold circuitry 42 is coupled to the energy storage device 16 for monitoring particular events. For example, the reset and threshold circuitry 42 may reset the controller 18 as the energy storage device 16 is recharging. This "power-on" reset function may occur when the capacitor voltage of the energy storage device 16 reaches a predetermined charging voltage, e.g. 3.8 V. In addition, during operation of the implant 10, the reset and threshold circuitry 42 may automatically turn the controller 18 and/or other components of the implant 10 off when the capacitor voltage of the energy storage device 16 drops below a predetermined shut-down voltage, e.g., 1.5 V.

The reset circuitry 42 preferably monitors the voltage of the energy storage device 18 in a substantially passive manner. For example, the reset circuitry 42 may include a fieldeffect transistor (FET) that is switched on when its gate voltage exceeds a predetermined threshold. Thus, the reset circuitry 42 may be passive, i.e., drawing substantially no current from the energy storage device 16.

The signal detect circuitry 44 generally is coupled to the energy transducer 16 for monitoring when the energy transducer 16 is receiving acoustic signals from a source external to the implant 10. Preferably, the signal detect circuitry 44 is a passive FET circuit, thereby drawing substantially no current. The signal detect circuitry 44 may also include a smoothing capacitor (not shown) and/or logic for reducing the sensitivity of the signal detect circuitry 44 to spurious transient signals. The signal detect circuitry 44 may provide a communication channel into the implant 10, e.g., to pass commands and/or information in the acoustic excitation signals received by the energy transducer 16 for use by the controller 18. In addition, the signal detect circuitry 44 may pass commands or other signals to controller 18, e.g., that acoustic excitation signals have been discontinued, and/or that the implant 10 should become operative. For example, when the implant 10 is configured for operation in half-duplex mode, the signal detect circuitry 44 may monitor for termination of an energizing transmission for charging the energy storage device 16, whereupon the controller 18 may begin sampling and/or transmitting sensor data.

The transmission circuitry 46 is coupled to the energy transducer 14, and is generally responsible for preparing signals for transmission from the implant 10 to a location exterior to the implant 10. The signals are preferably digital electrical signals, which may be generated, for example, by grounding one pin of the energy transducer 14 and alternately connecting the other pin between ground and a predetermined voltage. Alternatively, the signals may be generated by alternately grounding the first pin and connecting the second pin to the predetermined voltage, and then grounding the second pin and connecting the first pin to the predetermined voltage. In a further alternative, the signal may be processed or modulated, e.g., using spread spectrum, direct sequence mixing, CDMA, or other technologies, as will be appreciated by those skilled in the art.

Figure 11:
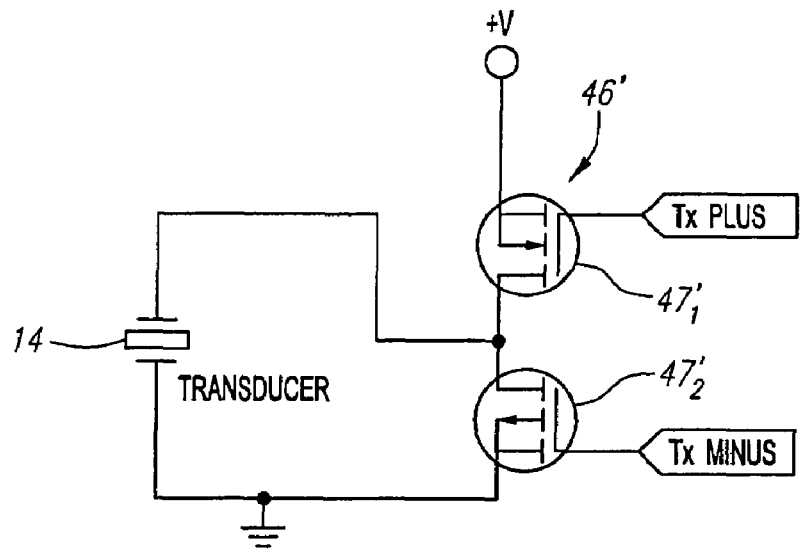
FIG. 11 is a schematic of an exemplary embodiment of a transmission circuit for use with an implant, such as that shown in FIG. 7.

FIG. 11 shows an exemplary embodiment of a transmission circuit 46' that may be used for transmitting such digital signals. The energy transducer 14 is coupled to ground and between a pair of transistors $47_1'$ and $47_2'$. The gates of the transistors $47_1'$ and $47_2'$ may be coupled to the control logic circuitry 52 (shown in FIG. 7) for receiving signals for transmission, such as sensor data signals from the sensor 12 (also shown in FIG. 7). Alternatively, the gates may be coupled directly to the analog-to-digital converter 50 (also shown in FIG. 7) or to the sensor 12. The incoming sensor data signals may alternatively couple the energy transducer 14 between ground and +V, thereby converting the sensor data signals into acoustic energy, which may be transmitted to a location exterior to the implant 10.

Figure 12:
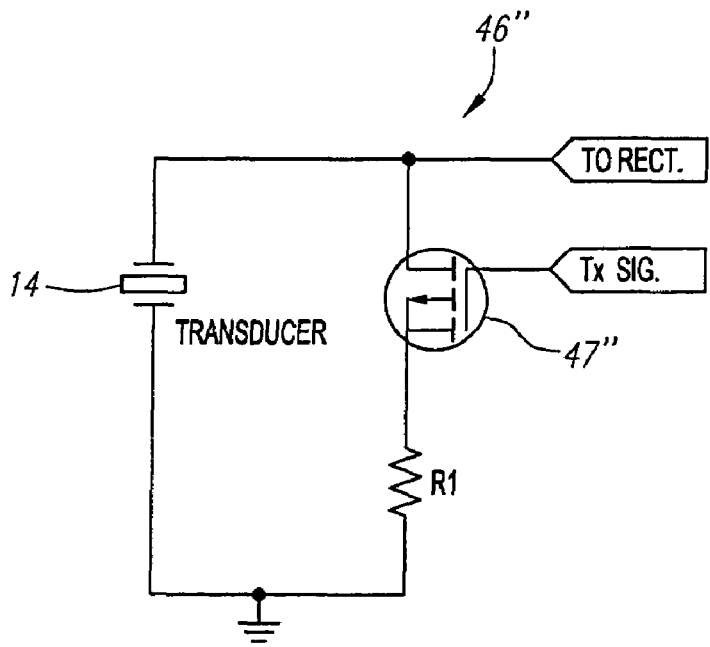
FIG. 12 is a schematic of another exemplary embodiment of a transmission circuit for use with an implant, such as that shown in FIG. 7.

FIG. 12 shows another embodiment of a transmission circuit 46" that may be provided for full-duplex operation, i.e., for simultaneously receiving an energizing signal and transmitting a data signal. For example, the energy transducer 14 may receive an energizing signal at a first frequency $f_1$, while the transmission circuit switches the transistor 49 on and off at a second frequency $f_2$, e.g., using sensor data signals. This periodic switching induces a current in the energy transducer 14 at frequencies $f_1+/-f_2$ and possibly others. This current causes the energy transducer 14 to transmit acoustic signals at the new frequencies, which may be correlated back to the sensor data by a receiver exterior to the implant 10. In a further alternative, the transmission circuitry 46 may include analog circuitry for generating analog signals that may be transmitted by the energy transducer 14.

In an alternative embodiment (not shown), a full-bridge transmission circuit may be used for the transmission circuit. Using this circuit, pins of the energy transducer may be coupled alternately to ground and +V. For example, a first pin may be coupled to ground and a second pin coupled to +V, and then the first pin may be coupled to +V and the second pin coupled to ground. This circuit may generate signals at about twice the amplitude of the other embodiments described above.

Returning to FIG. 7, the clock oscillator 48 may provide timing and/or clocking signals for the controller 18 and/or the various components of the implant 10. For example, the clock oscillator 48 may generate signals at fixed frequencies between about twenty and sixty kilohertz (20-60 kHz).

The analog-to-digital (A/D) converter 50 is coupled to the sensor 12, and to the control logic circuitry 52 or directly to the transmission circuit 46. The A/D converter 50 may digitize the sensor output for further processing by the controller 18 and/or for transmission by the energy transducer 14, using one of a variety of known digitization systems. For a variable capacitance pressure sensor, a switched-capacitor sigma-delta converter may be provided. Alternatively, for piezo-resistive or strain-gauge sensors, a track and hold amplifier followed by a successive approximation converter may be provided.

The A/D converter 50 may also include a calibrated voltage reference, against which measurements may be performed. Preferably, this is a bandgap reference, based upon the properties of silicon transistors. Alternatively, other reference circuits, such as Zener or buried Zener diode references, may be used.

The power management and control logic circuitry 52 may include several subsystems, such as a power management unit, a reception decoder, a transmission encoder, a state machine, and/or a diagnostic unit (not shown), which may be discrete hardware components and/or software modules. For example, an ASIC-compatible microprocessor, such as a CoolRISC processor available from Xemics, may be used for the power management and control logic circuitry 52. The power management unit may be provided for switching current on and off and/or for biasing voltages of the various components of the controller 18, particularly for any analog subcircuits, on demand. Thus, power may be supplied only to those portions or components currently in need of power, in order to conserve resources of the implant 10. The reception decoder is coupled to the signal detect circuitry 44 for decoding signals extracted by the signal detect circuitry 44 into commands to be passed to other components of the implant 10. These commands may include initialization, identification, control of system parameters, requests for sensor data or other information, and the like.

The transmission encoder is coupled to the transmission circuitry 46 and generally latches digital information supplied by the A/D converter 50 and prepares it for serial transmission by the transmission circuitry 46. The information may include an acknowledgement symbol, an identification code (e.g., a model, a serial number, or other identifier identifying the implant 10), internal status information (such as capacitor voltage), and/or measurements obtained by the sensor 12. Data may be sent using an asynchronous serial protocol, including, for example, a start bit, one or more synchronization bits, eight bits of data, a parity bit, and/or a stop bit. The data transmission rate and bit structure are preferably constructed so as to avoid data corruption due to reflections and reverberations of the acoustic signal within a body. For example, each bit of information may be made up of sixteen oscillations of the acoustic wave in order to ensure fidelity of the transmission. In addition, there may be predetermined delays between sequential transmissions, e.g., to minimize interference and/or to allow reverberations to die out.

The state machine controls the operational mode of the control logic circuitry 52. For example, it may determined the current mode (e.g., idle, decode, sample, transmit, and the like), and may contain logic for switching from one mode to another.

The diagnostic unit may include circuits used during manufacturing and/or calibration of the implant 10. This unit may not be operational after system integration, but may be awakened periodically by external command, e.g., to conduct in-vivo system diagnostics.

Turning to FIG. 6, to manufacture an implant 10, in accordance with the present invention, the various components may be assembled onto a double-sided printed circuit board (PCB) 11. The PCB 11 is preferably made from FR4 or other materials commonly used in the semiconductor industry, such as polyamide, Rogers, a ceramic, or Teflon™. The PCB 11 may have a thickness of between about ten and one thousand micrometers (10-1000 µm), and preferably about 0.25 millimeter (mm) or less. The sensor 12 and controller 18 may be flip chip bonded or wire bonded to one side of the PCB 11, e.g. using anistropic glue, a conductive adhesive, a nonconductive adhesive, or solder bumps. The active sensing area of the sensor 12 may be exposed through an opening 13 in the PCB 11, since the sensing area may be disposed on the same side as the electrical pads (not shown).

Alternatively, a single-sided PCB may be used, which may result in an implant that has a smaller thickness, but which may be longer or wider to accommodate the circuits printed thereon. A longer, thinner implant may be useful for implantation in particular locations within a patient's body, as will be appreciated by those skilled in the art. In a further alternative, a single-sided or double-sided flexible PCB may be used, e.g., having a thickness of about twenty five micrometer (25 µm). After assembly, the PCB may be folded, rolled, or otherwise arranged to minimize its volume.

To protect the sensor 12 and/or to prevent drift, the sensor 12 may be covered with a protective coating, e.g., a moisture barrier (not shown). Preferably, the sensor 12 is coated with a relatively soft material, such as silicone (e.g., NuSil MED4161). This coating may substantially minimize the stiffness or stress that may be imposed upon the sensor 12, which may otherwise affect its sensitivity and stability. Other protective and/or moisture barrier layers may then be applied over this coating, such as a relatively thin metal layer and/or Parylene C, without significantly affecting performance of the sensor 12. After the sensor 12 is assembled and coated, it may be calibrated, for example, by trimming the controller 18, e.g., by fuse blowing, and/or by soldering or otherwise bonding trim resistors 17 to the print side of the PCB 11.

The energy storage device 16, preferably a capacitor, may be attached to an edge of the PCB 11, e.g., bonded using epoxy or other adhesive. Conductive glue may be used for electrical contacts. The energy transducer 14 is attached to the print side of the PCB 111, e.g., by bonding with conductive glue. Additional mechanical fixation may be achieved, if desired, using an additional adhesive, such as an epoxy, around and/or under the energy transducer 14. Alternatively, the energy transducer 14 may be bonded using a conductive epoxy for electrical pad areas, and a structural epoxy for areas away from the pads. When the energy transducer 14 is attached to the PCB 11, the active area 15 of the energy transducer 14 is disposed away from the PCB 11 and/or otherwise exposed to transmit and/or receive acoustic energy, as described further below.

Preferably, a panel of implants are assembled, e.g., by attaching the components for multiple implants onto a single PCB. To calibrate the panel (or individual implants) following assembly, the panel may be inserted into a testing and diagnostic chamber (not shown). The chamber may be thermostatically controlled to ensure substantially constant temperature. In addition, pressure within the chamber may also be controlled within pressure ranges defined by the implants' specifications, e.g., pressure ranges to which the implants may be subjected during use. Preferably, the chamber includes a "bed of nails" or similar fixture (also not shown) that provides contact between desired electrical pads on the PCB and the conductive "nails." The nails are coupled to external diagnostic electronics that may perform diagnostics and calibration, e.g., via trimming, as required. Thus, the diagnostic electronics may communicate and/or control the implants on the panel via the nails. The testing generally includes calibration of the pressure sensors' sensitivity and offset, e.g., based upon comparison of measurements of the implants to a calibrated pressure sensor, and/or calibration of the frequency of the internal oscillator.

Once the panel has been assembled and/or calibrated, the panel may be separated into individual implants. For example, the panel may be diced using a milling machine, a dicing machine such as that used for dicing silicon wafers, a laser, or a knife-based cutter. If desired, an intermediate moisture barrier, such as Parylene C, may be applied to any or all of the components, e.g., the pressure sensor, the controller, etc., to provide additional protection for the covered components.

After separation, each implant 10 is generally placed within a box or other casing (not shown). The casing may protect the implant 10 from penetration of moisture or other body fluids, which may cause corrosion of the electrical pads or traces and/or may cause drift The casing may also provide mechanical protection and/or may provide connection points from which to attach the implant 10, e.g., to other devices that may also be implanted within a patient. The casing may be provided from titanium, gold, platinum, tantalum, stainless steel, or other metal. Alternatively, other biocompatible materials may be used, e.g., a polymer, such as a fluorocarbon, polyamide, PEEK, preferably covered with a metallization layer to improve the polymer's performance and/or to enhance its moisture resistance. The casing may also include a connector or other attachment fixture that may facilitate connecting the implant to other devices implanted within a patient's body, e.g., for receiving a suture that extends from a stent-graft or other implanted device.

Preferably, the casing is a five-sided box, and the implant 10 is disposed within the box such that the active areas of the sensor 12 and the energy transducer 14 are exposed through the open side. The implant 10 may be sealed within the box. For example, after assembly, a lid (not shown) may be attached to the sixth side, e.g., by welding, soldering, brazing, gluing, and the like. The lid may include openings corresponding to the active areas of the sensor 12 and/or the energy transducer 14, the perimeters of which may be sealed. Alternatively, a six sided casing may be used, having one side made of a relatively thin foil, e.g., only a few microns thick. In a further alternative, a six-sided compartment may be used, with one or more walls or one or more regions of walls being thinner than the others. The interior of the casing may be filled with a non-ionic solution, e.g., silicone oil, silicone gel, or other low modulus material, for coupling the pressure sensor and the energy transducer to the foil or thin-walled regions. U.S. Pat. No. 4,407,296 issued to Anderson, the disclosure of which is expressly incorporated herein by reference, discloses a casing that may be appropriate for use with an implant, in accordance with the present invention.

With the implant 10 within the casing, it may placed in a vacuum oven, e.g., at a temperature of about eighty degrees Celsius (80 C.) for outgassing, followed by plasma treatment for surface activation. The implant 10 may be attached to the casing using an adhesive, such as an epoxy, or silicone. The outer surface of the assembled casing and implant may be covered with a layer of Parylene C for improving corrosion resistance, a polymer to improve biocompatibility, and/or a metal deposition layer to provide a final moisture barrier. Preferably, a metal coating may be applied, which may electrically ground the casing with the energy transducer 14, and then a final coating of Parylene C or other corrosion resistance coating may be applied.

Figure 13A:
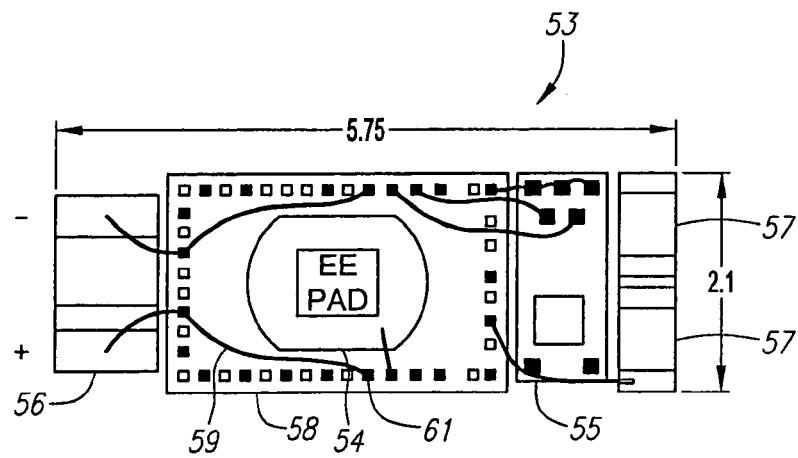
FIG. 13A is a top view of an another embodiment of an implant, in accordance with the present invention.
Figure 13B:
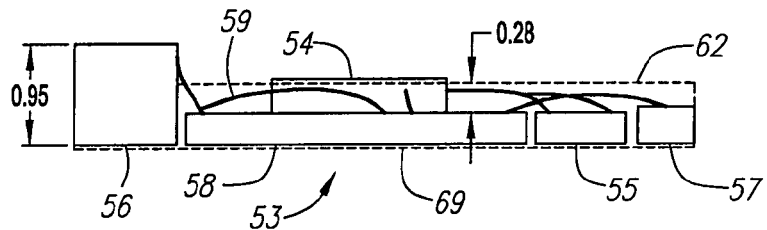
FIG. 13B is a side view of the implant of FIG. 13A.

Turning to FIGS. 13A and 13B, in an alternative embodiment, an implant 53 may be assembled using wire bonding rather than the flip-chip process described above. Similar to the previous embodiment, the implant 53 generally includes a sensor 55, one or more energy transducers 54, one or more energy storage devices 56, and a controller 58, which may include any of the subsystems or components described above. The implant 53 may be mounted within a casing (not shown), which may be formed from Titanium or other material, similar to the previous embodiment. In the exemplary embodiment shown, the overall dimensions of the implant 53 may be not more than about 5.75 mm long, 2.1 mm wide, and 0.95 mm deep. The casing may have a width about 0.1 mm wider than the widest component, e.g., the controller 58, and a depth of about 1.3 mm. Of course, these dimensions are only exemplary and may be varied to accommodate different size components or to facilitate implantation within predetermined locations within a patient's body.

During assembly, the sensor 55, the energy storage device(s) 56, and the controller 58 may be attached to the casing, e.g., to a bottom panel 69 (shown in phantom in FIG. 13B). After fabricating the energy transducer(s) 54, e.g., using the methods described above, the energy transducer(s) 54 may be attached to the controller 58, e.g., to an upper surface, as shown. The energy storage device(s) 56, e.g., one or more capacitors, may be coated, e.g., to electrically isolate the positive terminal and/or other portions of the energy storage device(s) 56.

Wires 59 may be bonded to provide any required electrical connections between the components, e.g., between the sensor 55, the energy exchanger(s) 54, the energy transducer(s) 56, and/or the controller 58. For example, the components may include one or more electrical contacts 61 to which ends of respective wires 59 may be soldered or otherwise bonded using known methods. The wires 59 may be bonded before testing the controller 58, e.g., in order to test operation of the entire implant 53. Alternatively, the wires 59 may be bonded after testing the controller 58 and/or other components individually or at intermediate stages of testing. For example, testing, calibration, and/or trimming the controller 58 may be completed using a probe card (not shown) that may be coupled to leads on the controller 58, e.g., similar to the bed of nails described above. During or after testing, trim resistor(s) 117 may be attached to the bottom 69 of the casing and/or electrically coupled to the controller 58 or other component. The trim resistor(s) 57 may be electrically isolated from the other components.

The subassembly may be cleaned and/or coated, similar to the previous embodiment. For example, the entire subassembly may be coated with Parylene or other moisture barrier. The sensor may be coated, for example, with silicone (NuSil), which may still expose an active area of the sensor, e.g., a membrane of a pressure sensor, to body conditions. Ground connections may be made, e.g., for the trim resistors 57 and/or other components. The casing may then be at least partially filled with potting compound, e.g., using a mold to protect the active area of the sensor 55. Preferably, the potting compound is filled to line 62 (shown in phantom in FIG. 13B), thereby covering all of the components, except the active area of the sensor 55 and/or the active area of the energy transducer(s) 54.

A lid, membrane, or other seal (not shown) may be attached to the casing to protect the implant 53 from an exterior of the casing, while still coupling the active areas of the sensor 55 and/or the energy transducer 54 to the exterior, similar to the previous embodiment. The space within the casing above the potting compound 62 may be filled with a fluid to acoustically couple and/or otherwise couple the active areas to the lid, membrane, or other seal. The lid may be attached first to the energy transducer 54 and then may be secured across an open end of the casing and/or the lid may be welded to the casing open end using a laser, electron beam plasma, magnetic welding, or any other welding method. The welding may be performed in a gas environment, preferably an inert gas (e.g., helium or argon), or while the parts are immersed within a fluid. Alternatively a thin membrane may be chemically etched or diffusion bonded to the lid.

Wire bonding may have advantages over the flip-chip process described above. For example, wire bonding may eliminate need for the PCB 11, and may allow the pressure sensor or other sensor to be mounted face up within the casing, which may simplify assembly. In addition, wire bonding may allow the implant 53 to be narrower in width and/or shorter in length than the previous embodiment. Because of the elimination of the PCB 11, the implant 53 may be easier, less expensive, and/or faster to assemble.

Figure 14:
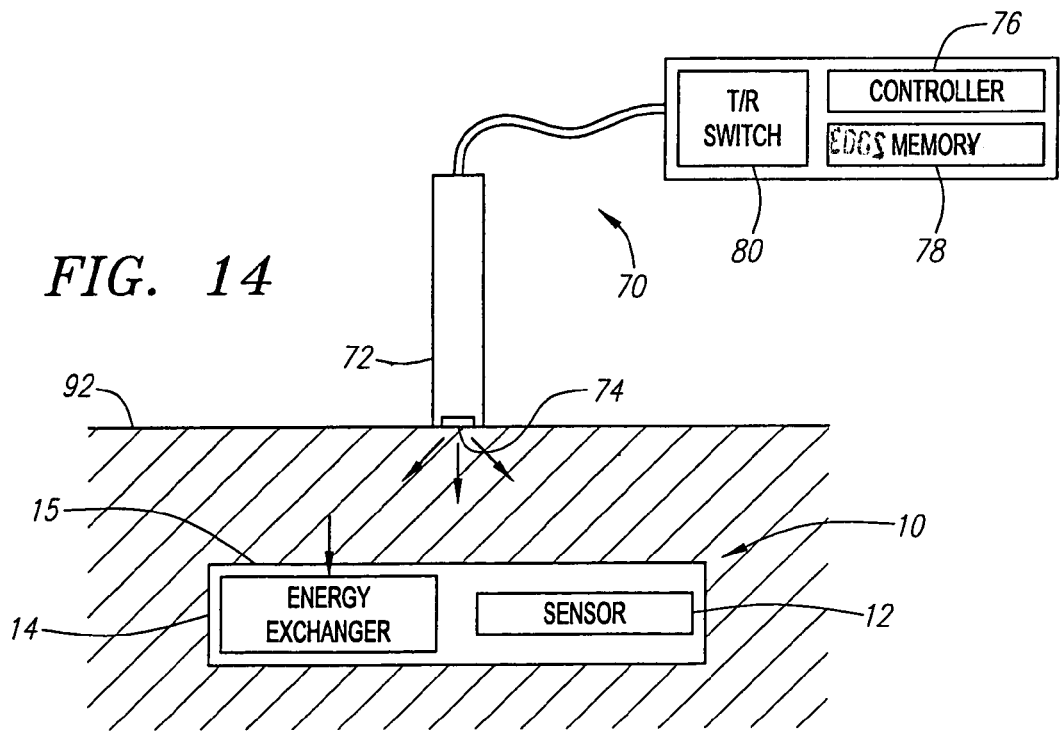
FIG. 14 is a cross-sectional view of a patient's body, showing an external device communicating with an implant located within the patient's body.

Turning to FIG. 14, during operation of an implant in accordance with the present invention, such as the implant 10, e.g., upon implantation within a patient's body 90, the implant 10 may be configured to operate in a "half-duplex" mode. In this mode, an external transducer 70 located outside the patient's body 90 may be used to control, charge, and/or communicate with the implant 10. The external transducer 70 includes a probe 72 having one or more energy transducers 74, e.g., similar to the energy transducer of the implant 10, for converting energy between acoustic energy and electrical energy. The external transducer 70 also generally includes control circuitry 76, memory for storing data 78, and a transmitting/receiving (T/R) switch 80, which may be separate from, but coupled to, the probe 72, or may be within the probe (not shown). The T/R switch 80 may toggle the energy transducer 74 to operate in one of two modes, an energizing mode for charging or activating the implant 10, and a receiving mode for receiving data from the implant 10. As described below, the external transducer 70 may automatically switch between these two modes one or multiple times during use.

First, the probe 72 may be coupled to the patient, e.g., placed against the patient's skin 92, and the energy transducer 74 operated in the energizing mode, transmitting acoustic energy from its energy transducer to the implant 10 through the patient's body 90. The acoustic energy from this energizing transmission passes through the patient's body 90, at least some of the energy striking the active area 15 of the energy transducer 14 of the implant 10. The energy transducer 14 converts the acoustic energy into electrical energy, e.g., which may be used to charge the energy storage device (not shown) or otherwise operate the implant 10, and/or to receive commands from the external transducer 70, as explained further below.

Initially, the external transducer 70 may be operated in a diagnostic mode. For example, the external transducer 70 may transmit a broadband signal or a scanning signal, i.e., scanning through a range of frequencies, and wait for the implant 10 to respond. The implant 10 may transmit at different frequencies in response to the diagnostic signal, and the external transducer 70 may determine the optimal frequency for communicating with the implant based upon the responses. For example, the external transducer 70 may repeatedly charge the implant 10 using different frequency signals and measure the length of time that the implant 10 is capable of sampling and transmitting data signals at each frequency to determine the optimal frequency. Alternatively, when the implant 10 detects the signal, it may transmit a response, the response being at an optimal frequency that should be used to communicate with the implant 10.

Once the external transducer 70 has determined the optimal frequency for communicating with the implant 10 (or the external transducer 70 may already know the proper frequency to use), the external transducer 70 may then begin its operation in energizing mode, transmitting acoustic energy from its energy transducer 74 through the patient's body 90 to the implant 10, which is stored in the energy storage device. The energy storage device may continue to store energy until a predetermined voltage is achieved, e.g., about eight Volts (8 V), and then the controller (not shown) may automatically disconnect the energy storage device from the energy transducer 14. Alternatively, the energy storage device may continue to store energy until a stop command is transmitted by the external transducer 70.

After a predetermined time, e.g., between about five and sixty seconds (5-60 sec.), the external transducer 70 may automatically cease the energizing transmission. At the end of the energizing transmission, the external transducer 70 may send an identification code, e.g., a predetermined pulse sequence, identifying a specific implant. In addition, the external transducer 70 may send a stop command, an activation command, a sampling rate instruction, or one or more other instructions. The external transducer 70 may then automatically switch to receiving mode and await data transmission from the implant 10 matching the identification code. Alternatively, the external transducer 70 may be switched manually to its receiving mode.

The controller of the implant 10 may detect the end of the energizing transmission and the identification code. The controller may confirm that the identification code matches the implant 10, and automatically activate the implant 10. Alternatively, the controller may acquire an activation command or other instructions from the external transducer 70, such as a sampling rate and the like, and activate in accordance with the instructions.

For example, once activated, the implant 10 may draw electrical energy from the energy storage device, and begin to sample data using the sensor 12. The controller may receive signals, e.g., raw pressure readings, from the sensor 12, digitize and/or otherwise process the signals, and transmit sensor data using the energy transducer 14. For example, the A/D converter may convert the raw pressure readings into digital data signals, which may be further processed by the controller in preparation for data transmission. The energy transducer 14 may convert the processed digital data signals from the controller into acoustic energy that may be transmitted through the patient's body 90 to the external transducer 70.

The implant 10 may continue to sample data and transmit the data signals until the voltage of the energy storage device 16 falls below a predetermined threshold, e.g., below a level at which the pressure sensor may not continue to operate effectively, such as 1.5 volts. For example, using a 4.7 µF tantalum capacitor for the energy storage device 16, the implant 10 may operate for between about two and six seconds (2-6 sec.). After the voltage falls below the predetermined threshold, the controller may automatically discontinue operation of the implant 10 and return to a passive state until energized and activated by the external transducer. The controller may also include additional information in the data transmission, e.g., an initial confirmation of instructions received from the external transducer, an identification code identifying the implant 10, and/or a stop notice when the signal transmission is being discontinued.

Thus, the external transducer 70 and one or more implants within the patient may operate in a cooperative manner. The external transducer 70 may energize one or more implants with an energizing transmission and/or may send instructions to individual or multiple implants. Thus, the external transducer 70 may selectively activate and receive data from one or more implants. The activated implant(s) may acquire data, transmit data signals to the external transducer 70 as acoustic energy, and then automatically return to their passive mode awaiting further instructions. The external transducer 70 may receive data from the one or more implants, which may be stored in memory 78 of the external transducer 70 or transferred to other equipment for use by medical personnel and the like.

In an alternative embodiment, the energy storage device may include a first relatively fast-charging capacitor and a second relatively slow-charging capacitor (not shown). For example, the first capacitor, which may be a relatively low-value capacitor, may be coupled to the energy transducer 14 initially, and, once the first capacitor is charged, the second capacitor, which may be a much higher value capacitor, may then be coupled to the energy transducer 14. In addition, once the first capacitor is charged, the controller may automatically transmit a signal to the external transducer, thereby opening a communication channel with the external transducer, e.g., identifying the implant 10, identifying its optimal communication frequency, and the like.

For example, the first capacitor may charge in about fifty to two hundred milliseconds (50-200 ms), thereby allowing the implant to respond promptly upon detecting a signal from an external transducer, e.g., within about fifty to two hundred milliseconds (50-200 ms). The charge retained by the first capacitor, however, may only allow the implant 10 to transmit a short reply, e.g., an identification code or other one or two word acknowledgement, in response to an interrogation from the external transducer. The second capacitor may retain a more substantial charge, e.g., that may be used to operate the implant 10 for more extended periods of time, similar to the embodiment described above.

In a further alternative embodiment, the external transducer 70 and implant 10 may operate in a quasi-continuous state, i.e., alternating between energizing/charging modes and transmitting/receiving modes. For example, the external transducer 70 may transmit an energizing transmission, e.g., for between about one and one hundred milliseconds (1-100 msec.), to charge the energy storage device with sufficient energy to operate the implant 10 for a predetermined time, e.g., several milliseconds. The external transducer 70 may then switch to receiving mode, and the implant 10 may become activated, as described above, and sample and transmit data. After the predetermined time, the implant 10 may automatically switch back to charging mode and wait for another energizing transmission from the external transducer 70. After receiving the data transmission from the implant 10, the external transducer 70 may switch back to the energizing mode and transmit another energizing transmission to recharge the implant 10. Thus, the process of "interrogating," i.e., requesting data from the implant 10, and transmitting sensor data may be repeated substantially indefinitely, as desired. For example, the external transducer 70 and implant 10 may operate at a predetermined duty cycle, e.g., at a rate of about fifteen to thirty Hertz (15-30 Hz), depending upon how much information is needed. This mode of operation may allow a smaller capacitor or other energy storage device to be used, while still allowing substantially continuous monitoring with no specific duration limit.

This quasi-continuous mode may also be implemented by the implant 10 in a hybrid mode. The external transducer 70 may transmit an energizing signal whenever the operation of the implant 10 allows. For example, when the implant 10 is obtaining and/or processing data or between bits being transmitted by the implant 10, the energy transducer 14 may be available to receive additional energy from the external transducer. These additional energizing signals may be used to "top off" the charge on the energy storage device, thereby substantially extending the length of time that the implant 10 may operate.

In a further alternative embodiment (not shown), the implant may be operated in full-duplex mode. To facilitate this mode, the energy transducer is generally configured to transmit at a different frequency than the data signal transmissions of the implant. This may be achieved by providing one or more separate energy transmitters and receivers in the external transducer. Alternatively, the external transducer may include a single energy transducer and a circuit for separating the data transmission frequency, similar to the transmission circuit shown in FIG. 12 and described above. Thus, the external transducer and the implant may both be configured for filtering and/or otherwise separating the two transmissions from one another. Full-duplex mode may allow the implant truly to operate continuously. Because the energy transducer of the implant may receive energy substantially continuously from the external transducer via the energizing transmission, the implant may sample and transmit data substantially indefinitely, if desired, or until a stop command is transmitted from the external transducer.

Although full-duplex mode allows continuous operation of the implant, the half-duplex mode also has advantages over the full-duplex mode. First, because of its higher efficiency, i.e., only activating components as they are needed, half-duplex mode may reduce the amount of energy consumed by the implant 10, allowing the implant 10 to operate at higher voltages, although for relatively short periods of time. Second, simultaneous energizing and transmitting in full-duplex mode may cause interference between the energizing and data signal transmissions. In particular, because the energizing transmission is much stronger than the data signal transmission, the energizing transmission may create background noise for the signal transmission. In half-duplex mode, the energizing and data signal transmissions are separated in time, increasing the fidelity and detection of the signal transmission. Finally, half-duplex mode may allow a single energy transducer to be used as both an energy exchanger and as a transmitter, simplifying construction of the implant and possibly reducing the amount of acoustic energy needed.

Having described various embodiments of an implantable biosensor and systems for communicating with implantable biosensors, barometric pressure correction for implantable devices will now be described. The methods and systems described herein can be used with any implantable or external device that can benefit from barometric pressure data or barometric pressure correction. In particular, we will describe the methods and systems as they are used in connection with an implantable biosensor or implantable patient monitor. But in addition to implantable biosensors and implantable patient monitors, the present systems and methods can also be used in conjunction with other implantable and external devices, such as pacemakers, ventricular assist blood pumps, implantable and external drug delivery pumps such as insulin pumps, infusion pumps, artificial hearts, lung machines, drug infusion and drug release devices activated with telemetric signals, defibrillators, neurostimulating devices, aortic assistant balloons, intra ocular shunts for controlling intra ocular pressure, intra cranial shunts, incontinence control devices, contrast media automatic injectors, impotence devices, etc.

Figure 15A:
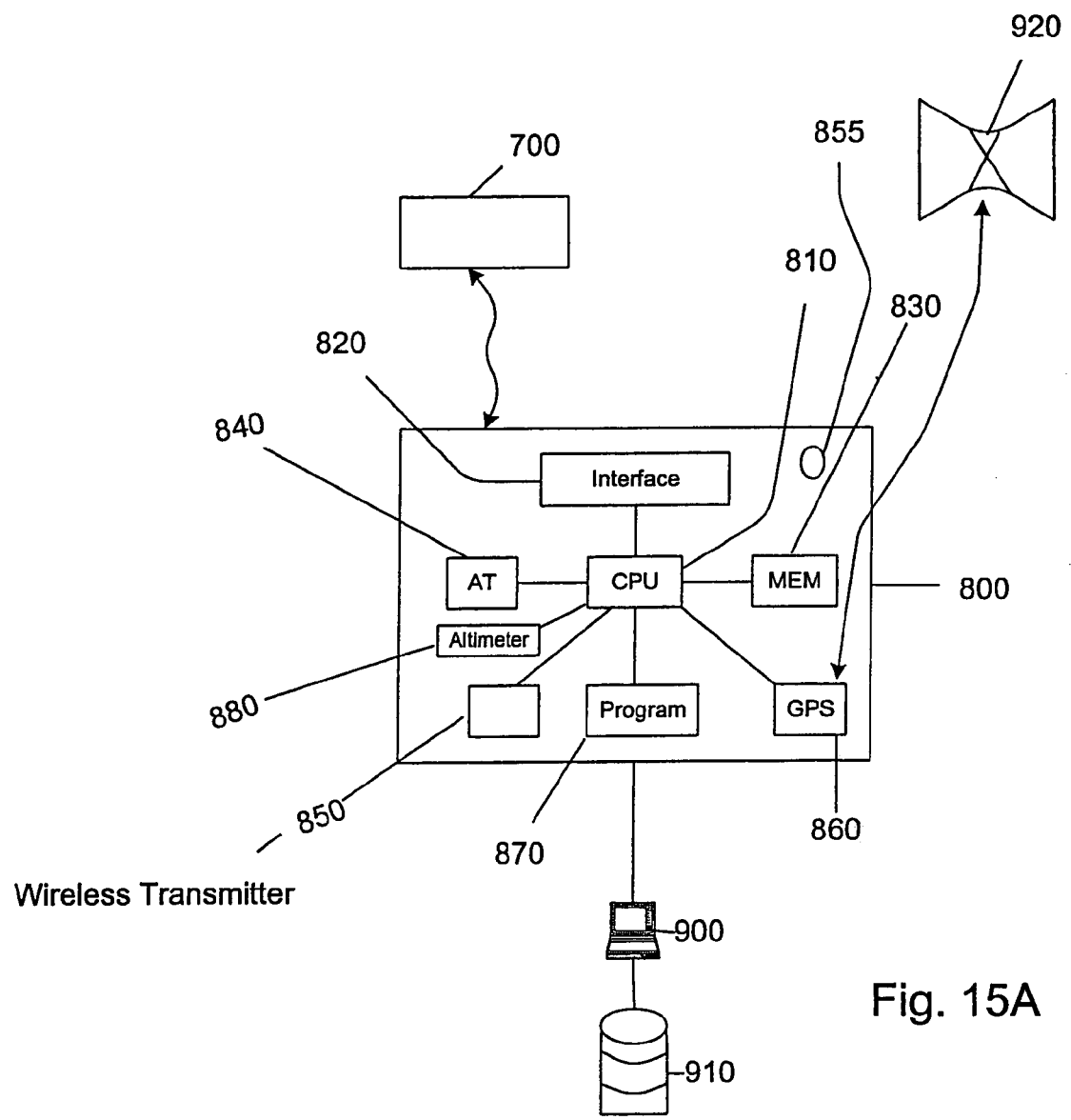
FIGS. 15A and 15B are diagrams of a barometric pressure correcting system in communication with a database having barometric pressure data according to one embodiment.

FIG. 15A shows a system for measuring pressure in a body by converting absolute pressure data acquired from an implantable biosensor to gauge pressure data. The system includes an implantable biosensor 700. The implantable biosensor 700 can be of any type, including those shown and described in FIGS. 1A-14. The implantable biosensor 700 is configured to obtain absolute pressure data within an anatomical structure, such as a blood vessel. The implantable biosensor 700 can include a pressure sensor and an internal controller coupled to the pressure sensor for acquiring absolute pressure data from the pressure sensor. The implantable biosensor 700 can also include an acoustic transducer for converting energy between electrical energy and acoustic energy. The acoustic transducer of the biosensor 700 can be configured to convert acoustic energy from an external monitor 800 into electrical energy to power the biosensor 700. The acoustic transducer of the biosensor 700 can include an acoustic transmitter for transmitting an acoustic signal to the external monitor 800. More particularly, it can be configured to transmit an acoustic signal comprising absolute pressure data to the external monitor 800. In addition, the acoustic transducer can include an energy exchanger coupled to an energy storage device. The energy storage device can be configured for storing electrical energy converted by the acoustic transducer from acoustic energy. In one embodiment, the biosensor 700 can include a processor for calculating gauge pressure based on the absolute pressure that it monitors and measures and barometric pressure information received from the external monitor 800. The biosensor 700 can transmit the pressure data, whether it be absolute pressure or gauge pressure to the external monitor using a telemetric signal.

The system shown in FIG. 15A can also include an external monitor 800, a GPS satellite communications system 920, a computer system or network 900, and a database 910 in communication with or stored in a memory of the computer system 900. The database 910 can include real-time barometric pressure data for numerous geographic locations throughout the world. The database 910 can alternatively be associated with a remote computer system, which can be accessed by the computer system 900, or directly by the external monitor 800 through a telecommunications link achieved through a wireless transmitter 850 or connector or lead (not shown) extending from the external monitor 800.

Figure 15B:
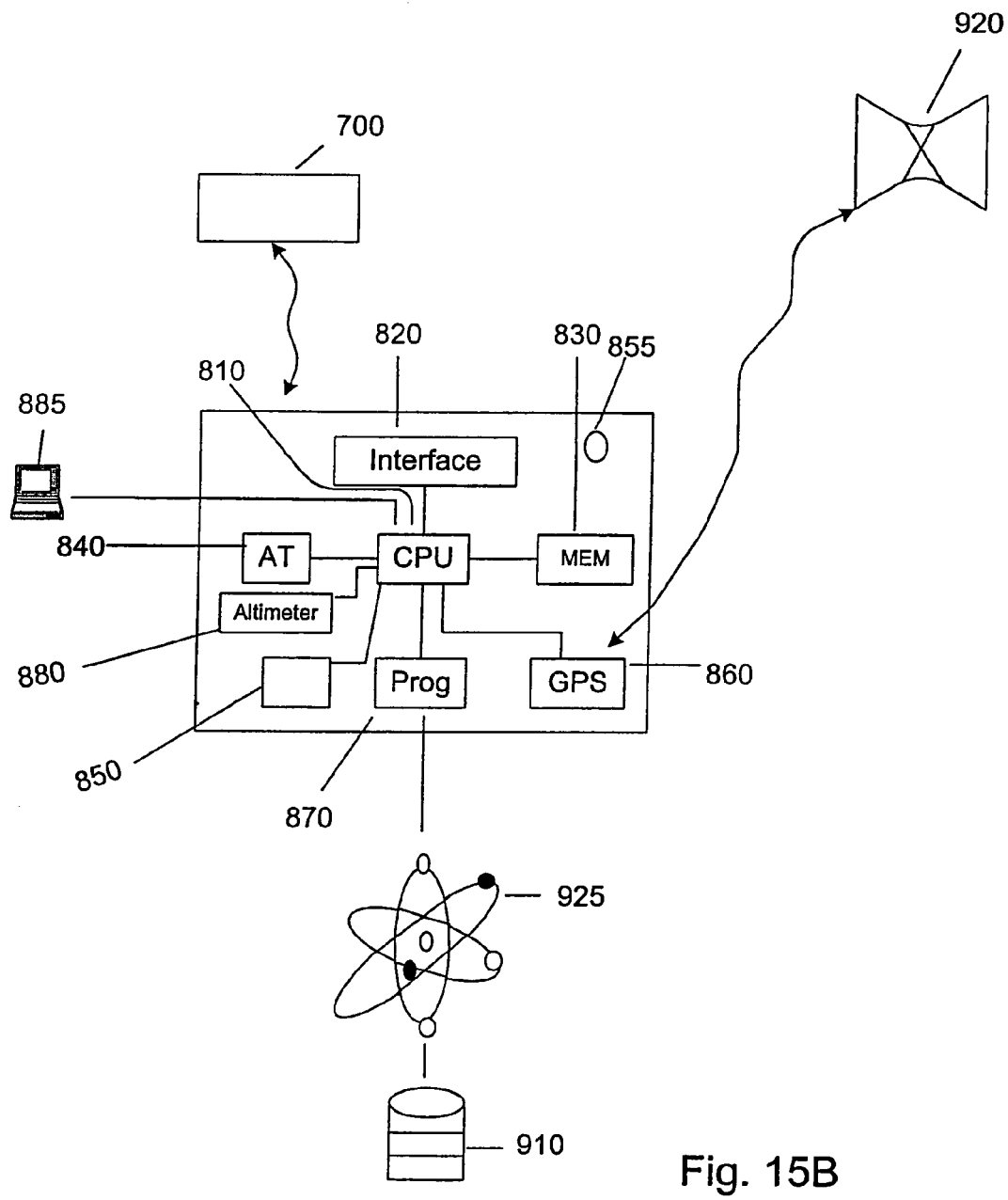

The external monitor 800 can be like any one of those external communications devices shown and described in FIGS. 1A-14 particularly FIGS. 3, 4, and 14. The external monitor 800 can be configured to receive absolute pressure data from the biosensor 700, real-time barometric pressure data from the database 910, or gauge pressure data calculated by the computer system 900 or other source. In addition, it can be configured to receive barometric pressure data from a barometer 885 (shown in FIG. 15B), through a lead or connector, or through wireless transmission of data through the wireless transmitter 850. Alternatively, the barometer 885 can be integrated into the external monitor 800 (not shown).

Preferably, the external monitor 800 includes a central processing unit or microprocessor 810. The microprocessor 810 can be configured to control an acoustic transducer 840, with which it is in communication. The external monitor 800 can include an energy source 855 for powering the external monitor 800, and particularly the acoustic transducer 840. The acoustic transducer 840 can be configured to convert acoustic signals received from the biosensor 700, which can represent inter alia absolute pressure data, into electrical signals. The acoustic transducer can transmit the electrical signals to the microprocessor 810 for processing and storage within a memory 830. Like the memory 424 described in relation to FIG. 4, the memory 830 may be a temporary buffer that holds data before transfer to another device, or non-volatile memory capable of storing the data substantially indefinitely, e.g., until extracted by the microprocessor 810 or other electronic device. The memory can be configured to store geographic location data, altitude data, temporal data, and pressure data.

The microprocessor 810 can also include a computer program, such as an Internet browser, which is configured for interfacing with the computer system 900, a global communications network, or an outside electronic device (not shown). The microprocessor can also include a computer program 870 configured to calculate gauge pressure data by subtracting barometric pressure data from absolute pressure data based on the following equation:

$$Pgauge = Pabs - Pbaro$$

where
Pgauge=gauge pressure
Pabs=absolute pressure
Pbaro=barometric pressure

The computer program 870 can also be configured to factor in altitude, which changes barometric pressure by about 1 mbar per every eight meters in altitude based on the following equation:

$$P(z) = P(sea\ level)^{-z/H}$$

where
P(z)=pressure at height z
P(sea level)=seal level pressure (~1013 millibars)
z=height in meters
H=scale height (i.e., RT/g)

Alternatively, the computer program 870 can be associated with a processor located in the biosensor 700. The external monitor 800 can also include an interface 820, which can include a keyboard or keypad. The interface 820 can also include a display for displaying pressure data, including absolute pressure data received from the biosensor 700, barometric pressure data received from the computer system 900, database 910, or barometer 885, or gauge pressure data.

The external monitor 800 can also include a GPS receiver 860 and an altimeter 880. Both the GPS receiver 860 and altimeter 880 can be coupled to or otherwise in communication with the microprocessor 810. The microprocessor 810 can be configured to process geographic location data and altitude data received from the GPS receiver 860 and altimeter 880. Both the geographic location data and altitude data can be stored in the memory 830. Alternatively, the GPS receiver 860 and satellite system 920 can be used to provide altitude data in addition to or in conjunction with geographic position data, in which case the altimeter 880 is unnecessary or can be integrated for redundancy.

The computer system 900 can be a personal computer, a local area network, a wide area network, or any other system, including one that includes an Internet connection. The database 910 can be one stored within a memory directly associated with the computer system 900 and constantly updated through manual input or automated retrieval of information through satellite or telecommunications links with external sources. The computer system 900 in turn can include a memory programmed with the location and altitude data associated with its temporary or permanent location and altitude. This data can be modified and the computer reprogrammed with new data whenever the computer system 900 is moved to a new location. Alternatively, the database 910 can be a remote database accessed by the computer system 900 through a global communications network The external monitor 800 can be connected to the computer system 900 through a wireless communications link achieved through the wireless transmitter 850, or through a lead or connector (not shown). Wireless communication between the components of the system, such as the external monitor 800 and computer system 900, may be accomplished or assisted using devices which conform to the BLUETOOTH standard, a 2.4 GHz wireless technology employed to transport data between cellular phones, notebook PCS, and other handheld or portable electronic gear at speeds of up to 1 megabit per second. Other suitable wireless communication standards and methods now existing or later developed are contemplated in the present invention.

In another alternative, if the database 910 is a remote database, the external monitor 800 can communicate with the remote database 910 through a telecommunications link 925 (shown in FIG. 15B) of its own rather than through the computer system 900. This can be achieved by the use of a mobile telephone or other electronic device (not shown) configured for wireless Internet access. The mobile telephone or other electronic device can be in communication with the external monitor 800 through the wireless transmitter 850 or a lead or connector (not shown). Alternatively, the link with the remote database 910 can be achieved through telecommunications hardware and software (not shown) built into the external monitor 800.

Figure 16:
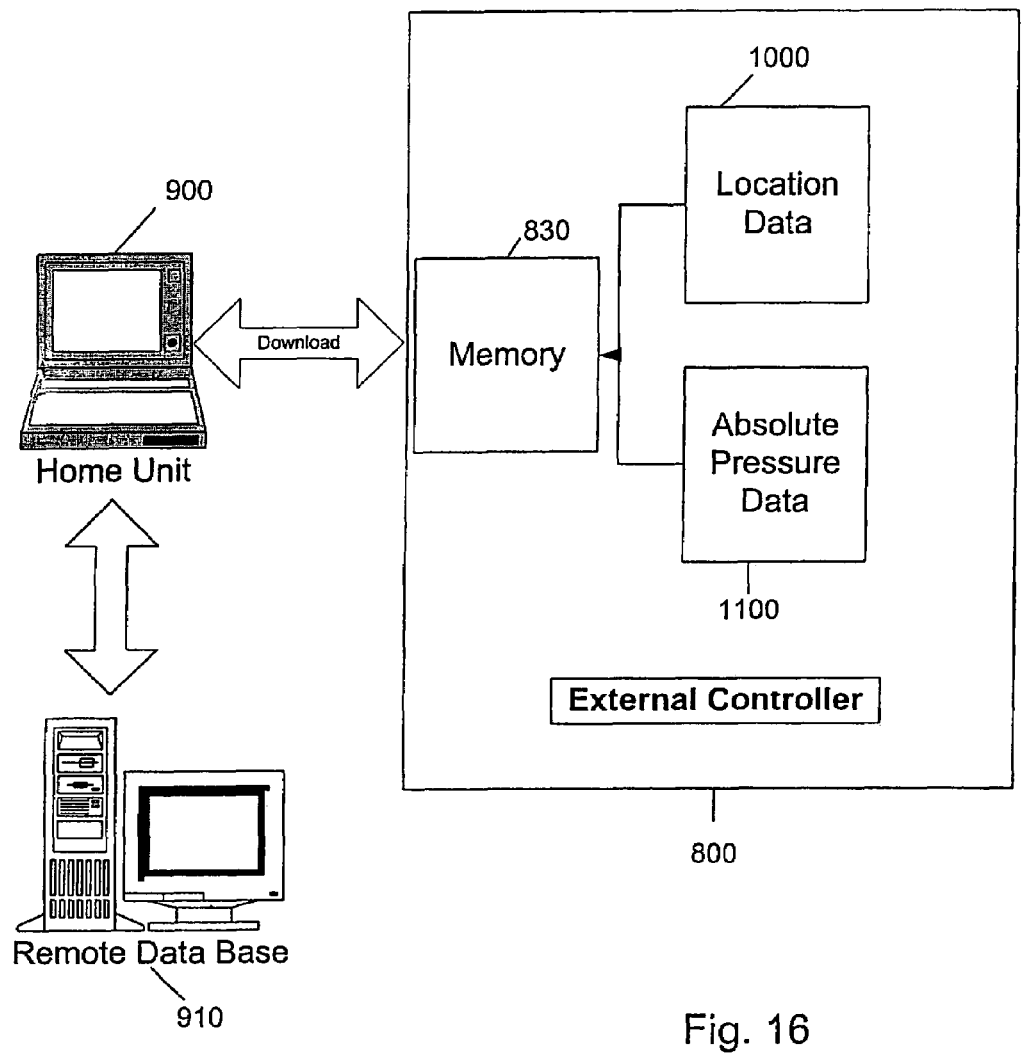
FIG. 16 is a block diagram depicting the flow of information in a barometric pressure correcting system according to one embodiment.

Now turning to FIG. 16, the external monitor 800 can receive absolute pressure data 1100 from the implantable biosensor 700 and can store it in memory 830. The external monitor 800 can obtain location/altitude data 1000 from a number of sources as described in more detail below, and can store that data in memory as well. The location and altitude data 1000 and the absolute pressure data 1100 can all be transmitted through a download to a computer system 900, which can be a home unit. The computer system 900 can be used to obtain real-time barometric pressure data from the remote database 910. The remote database 910, can be associated with an Internet weather web site, such as Yahoo® weather, Weather.com, or AWS.com, or it can be any database that includes real-time barometric pressure data for numerous locations throughout the world. The real-time barometric pressure data that the computer system 900 retrieves from the remote database 910 can correspond with the location of the external monitor 800 as represented by the location data 1000. The computer system 900 can include an algorithm to calculate gauge pressure based on the following two equations:

$$P_{gauge}=P_{abs}-P_{baro} \text{ and } P(z)=P(\text{sea level})^{-z/H}.$$

After calculating the gauge pressure including the altitude factor, the computer system 900 can trasmit the gauge pressure data to the external monitor 800, where the data can be displayed on the interface 820, or it can be stored for subsequent retrieval in memory 830. The computer system 900 can display the resulting gauge pressure data on its computer screen simultaneously with or in place of displaying it on the interface 820. The data can also be stored for subsequent retrieval in a memory of the computer system 900. Alternatively, the computer system 900 can transmit real-time barometric pressure data corresponding to the geographic location associated with the location data 1000 to the external monitor 800, which can then calculate gauge pressure by using the computer program 870, which can use an algorithm based on the same two equations shown above. The gauge pressure data can then be displayed on the interface 820, and it can also be stored indefinitely in the memory 830 for subsequent recall. In addition, the computer system 900 can be preprogrammed with predetermined location and altitude data. The external monitor 800 can then be used to call upon the computer system 900 to obtain real-time barometric pressure data from outside sources corresponding with the predetermined location associated with the predetermined location data.

Figure 17:
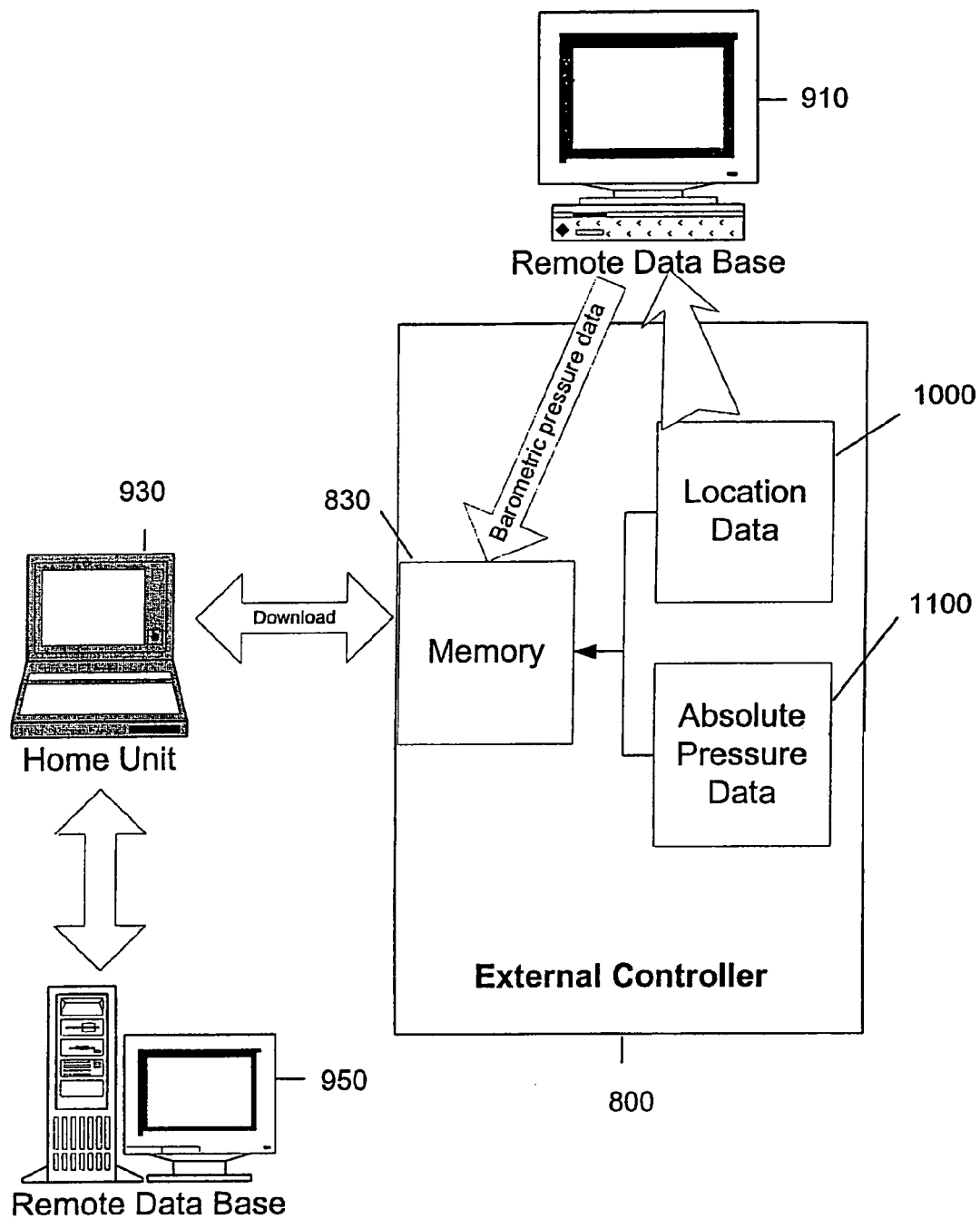
FIG. 17 is a block diagram depicting the flow of information in a barometric pressure correcting system according to another embodiment.

Alternatively, as shown in FIG. 17, the external monitor 800 can communicate directly with a remote database 910 having barometric pressure data. Again, the remote database 910 can be associated with an Internet weather web site, such as Yahoo® weather, Weather.com, or AWS.com, or it can be any database that includes real-time barometric pressure data for numerous locations throughout the world. To communicate with the remote database 910, the external monitor 800 can be coupled to a mobile telephone or other electronic device configured for wireless Internet access or access to the remote database 910. The external monitor 800 can also include the requisite hardware and software for wireless Internet access or wireless communication with the remote database 910, thus obviating the need for a mobile telephone or other external electronic device. Once in communication with the remote database 910, the external connector can send its location data 1000 to the database 910 and can request barometric pressure data for a location corresponding with the location represented by the location data 1000. The barometric pressure data is then received into the memory 830, whereupon the computer program 870 calculates gauge pressure data based upon the same two equations shown above. The resulting gauge pressure data can be displayed on the interface 826 and can be stored indefinitely in the memory 830 for subsequent recall. In addition, the location data 1000, absolute pressure data 1100, barometric pressure data, gauge pressure data, and altitude data can all be stored in the memory 830 separately, and they can be transmitted, either through a telecommunications link or a lead or connector, to a home unit 930 for permanent storage and subsequent recall. Alternatively, the home unit 930 can transmit the data to a database 950 for permanent storage and subsequent recall. The home unit 930 can be located at a facility controlled and/or monitored by, for example, a healthcare organization or doctor's office. Thus, the system enables rapid communication of pressure data, as well as any physiological parameters monitored by the biosensor 700, can be rapidly and automatically relayed to a doctor's office, which can store the information or use it for rapid deployment of emergency healthcare services to the patient.

The location data 1000, can be determined in a number of ways. In one embodiment, the GPS receiver 860 can obtain location data 1000 from a GPS satellite communications system 920. The GPS receiver can transmit the data to the microprocessor 810, which can process the data and store it in the memory 830. The GPS receiver 860 and GPS satellite communications system 920 can also determine altitude along with geographic location for a packet of position data corresponding with geographic position and altitude position.

Alternatively, the location data can be determined by the use of a zip code or telephone number along with altitude data acquired by an altimeter 840. The microprocessor 810 can include a database of zip codes and telephone number area codes and prefixes. The zip code or telephone number can be entered through a keypad associated with the interface 820 of the external monitor 800. The information can be transmitted to the microprocessor 810, which can process the information and obtain location data 1000 and then store it in the memory 830. Alternatively, the external monitor 800 can obtain location data 1000 by communicating—by any of the means described above—with a remote database (not shown) of zip codes or telephone numbers with associated location data. It can send a request for location data associated with the zip code or telephone number entered into the keypad, and it can receive the corresponding location data 1000, which it can then process and store in the memory 830. In yet another alternative, either of the computer systems 900 or 930 can include a database of zip codes or telephone numbers with associated location data. The external monitor 800 can transmit the zip code or telephone number to the computer system 900 or 930 and receive the corresponding location data 1000. In yet another alternative, a mobile telephone network system can be used to obtain location data. The external monitor 800 can be coupled to a mobile telephone (not shown), and can use the network associated with that mobile phone to obtain location data 1000. In another alternative, location data can be obtained by using a local network location system. With this embodiment, precise gauge pressure data can be calculated using the altitude data from the altimeter 840 factored into the geographic position data obtained using phone numbers, zip codes, mobile telephone network systems, or local network location system.

Figure 18A:
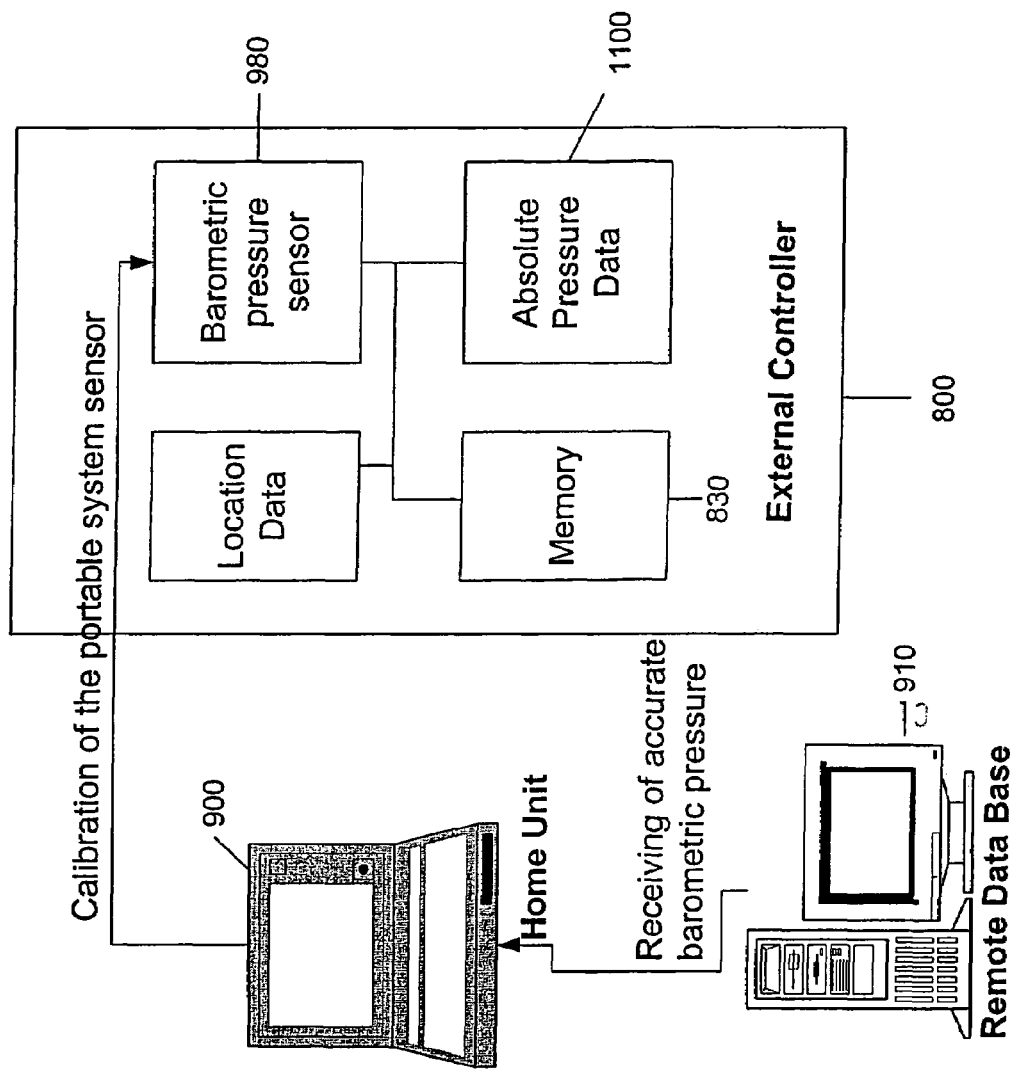
FIG. 18A is a block diagram depicting the flow of information in a barometric pressure calibration system according to another embodiment.

FIG. 18A shows another embodiment of the invention. In this embodiment, the external monitor 800 includes a barometer 980. Alternatively, the barometer 980 can be an external device that is coupled to the external monitor 800 with a lead or connector or is in close-range wireless communication with the external monitor 800. The barometer 980 can be calibrated using a remote database 910 having real-time barometric pressure data for numerous locations throughout the world. The external monitor 800 can obtain accurate barometric pressure data in any of the ways described with respect to FIGS. 16 and 17, which can include the use of a home unit 900.

Figure 18B:
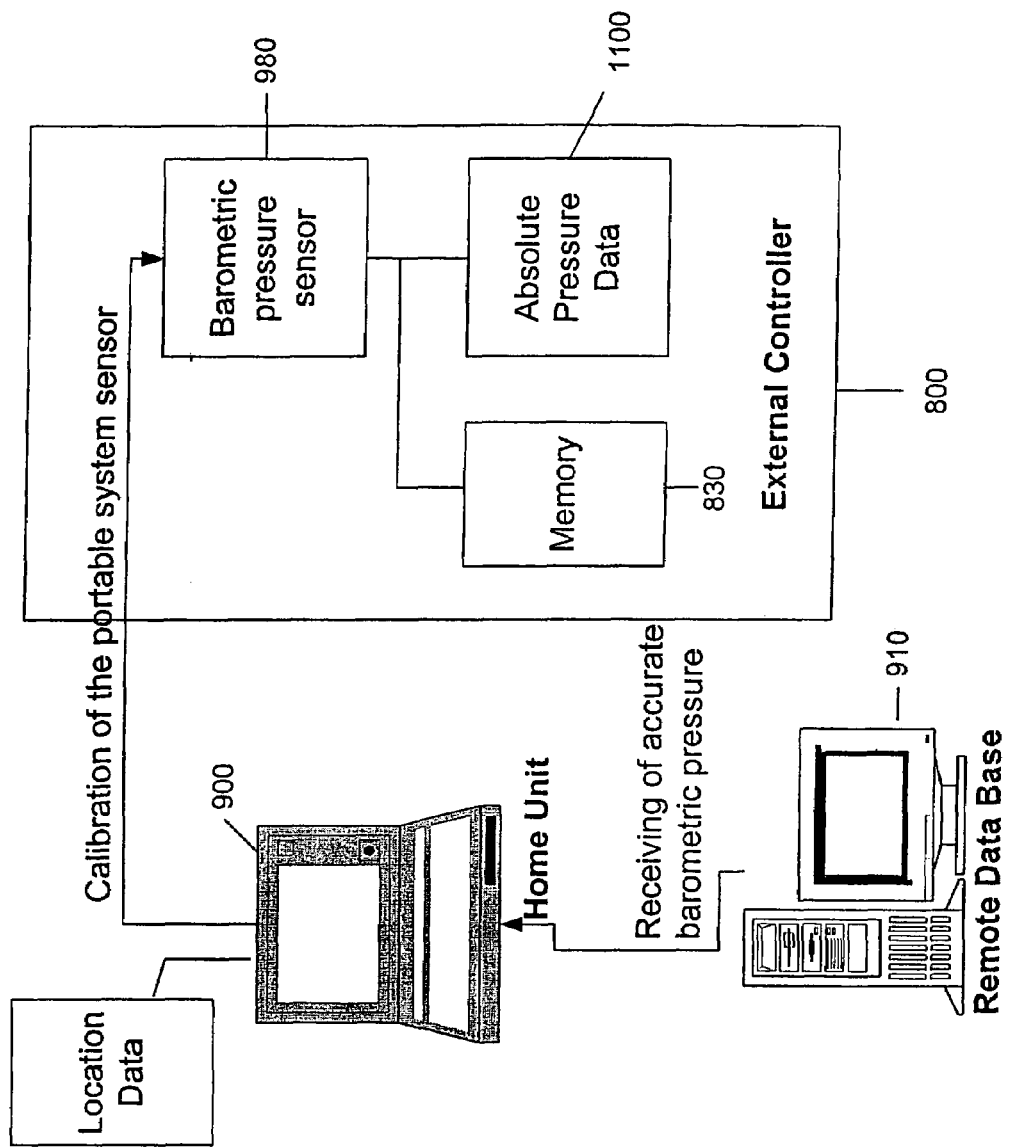
FIG. 18B is a block diagram depicting the flow of information in a barometric pressure calibration system according to another embodiment.

For example, in one embodiment as shown in FIG. 18B, the system can include a computer system 900 that is preprogrammed with geographic location and altitude data, which corresponds with its home location. This data can be modified whenever the computer system 900 is moved to a new location. The external monitor 800 can call upon the computer system 900 to retrieve real-time barometric pressure data from a remote database 910, such as any of those described above. The computer system 900 can then transmit that data to the microprocessor 810 of the external monitor 800, which can in turn transmit the data to the barometer for processing and automated calibration of the barometer. Alternatively (not shown), the microprocessor 810 can store barometric pressure data received from the barometer 980 in the memory 830. Using a calibration algorithm, the microprocessor 810 can use the data received from the remote database 910 to correct the data from the barometer 980. The location and altitude data can be obtained in the same ways as described with respect to FIGS. 16-18B.

Figure 19:
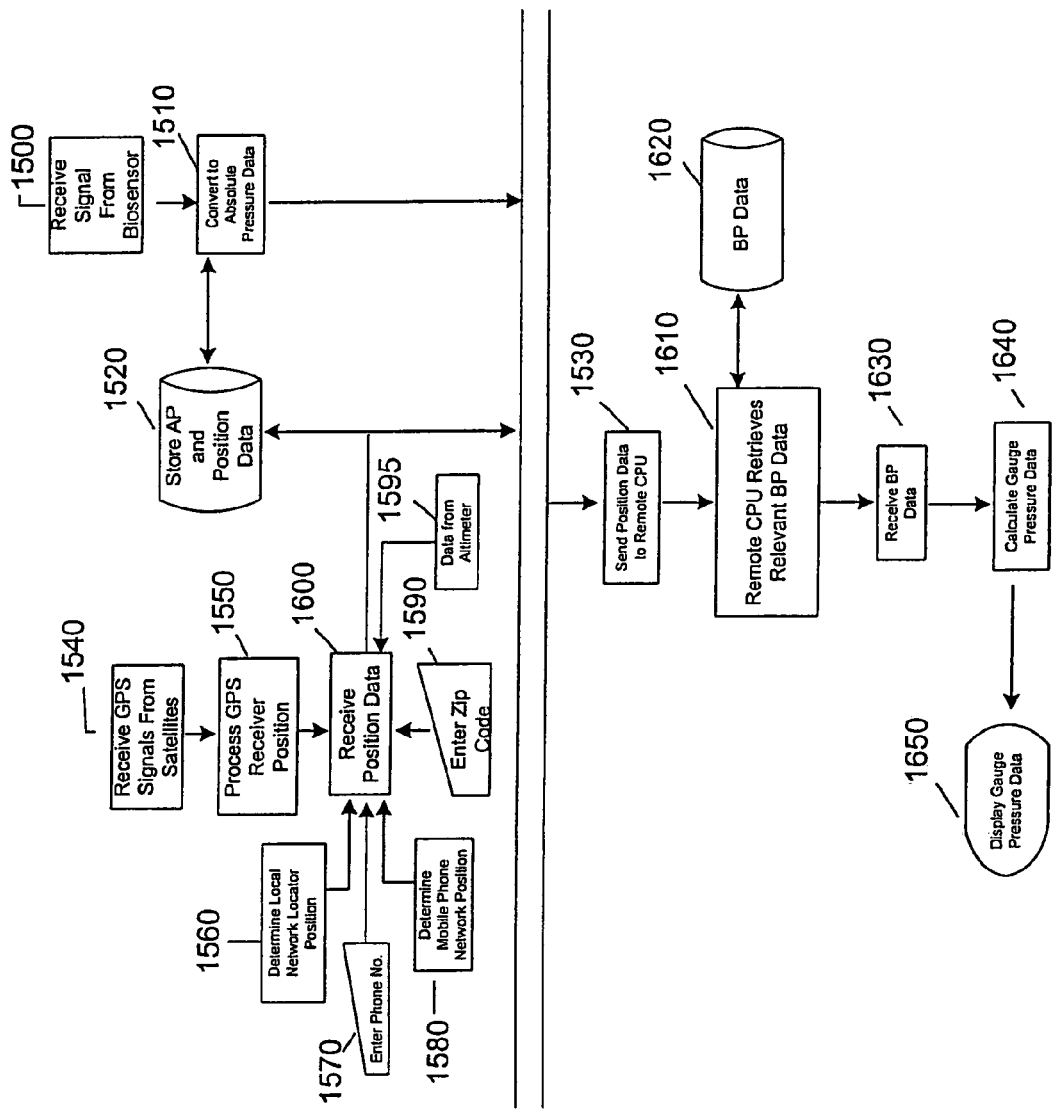
FIG. 19 is a flow chart of some embodiments of methods of the present invention.

FIG. 19 shows an embodiment of a method of correcting absolute pressure data received from an implantable biosensor to account for ambient (e.g., barometric) pressure. The method utilizes an external monitor 800, such as that described above, which is capable of performing the steps involved in the method. The method includes the first step of using the external monitor 800 to receive a signal 1500 from a biosensor 700. The signal can be any telemetric signal such as acoustic, RF, electromagnetic, microwave, light (e.g., infrared) or any other form of telemetric signal. The signal can represent absolute pressure data. The next step can be to convert the signal into absolute pressure data 1510, which can be stored 1520 in a memory 830. This step can be accomplished with a transducer, such as the acoustic transducer 840 described above, for converting the telemetric signal into an electric signal, optical signal, or any other signal that can be transmitted to a microprocessor 810 of the external monitor 800. The microprocessor 810 can then process and store 1520 the absolute pressure data in a memory 830.

In parallel fashion, the external monitor 800 can receive position data 1600 from various sources. The position data is then used to obtain real-time barometric pressure data corresponding with the geographic location represented by the position data. The steps of obtaining the appropriate real-time barometric pressure data from a remote microprocessor are performed at steps 1530, 1610, 1620, and 1630. In one embodiment, the external monitor 800 includes a GPS receiver 860. The GPS receiver can receive GPS signals 1540 from GPS satellites 920, and it can process geographic position and altitude data 1550, thus determining the location and altitude of the external monitor 800 and consequently the biosensor, which is in close proximity to the external monitor 800. Altitude data be obtained 1595 from an altimeter in addition to or in place of the GPS system, the altimeter being integrated with or otherwise coupled to the external monitor 800. Alternatively, the geographic position of the external monitor 800 can be determined using a local network location system 1560. In yet another alternative embodiment, the position of the external monitor 800 can be determined by using a mobile telephone network location system 1580. Alternatively, the position of the external monitor 800 can be determined by entering a phone number 1570 or a zip code 1590 into an interface 820 keypad located on the external monitor 800. The microprocessor 810 of the external monitor 800 can either process the appropriate position data associated with the phone number or zip code by searching an internal database of phone numbers and/or zip codes with corresponding geographic position data. Alternatively, upon receiving position data 1600, the microprocessor 810 can store it 1520 in a retrievable database, or it can send the position data to a remote microprocessor 1530 for use in retrieving relevant barometric pressure data 1610. If the geographic position data represents a telephone number or zip code rather than geographic position data, the remote microprocessor 810 can search its own database of phone numbers and zip codes for corresponding geographic location data. Alternatively, it can search an online database of telephone numbers and zip codes for corresponding geographic position data. The geographic position data is used by the remote microprocessor to select barometric pressure data corresponding with the geographic location represented by the geographic position data. Thus, the remote microprocessor searches a database of real-time barometric pressure data 1620, retrieves the appropriate data 1610, and sends it to the microprocessor 810 of the external monitor 1630, which consequently receives that data. The microprocessor 810 of the external monitor 800 can include an algorithm for calculating gauge pressure from absolute pressure using barometric pressure and altitude data. The calculation involves the following equations:

$$Pgauge = Pabs - Pbaro \text{ and } P(z) = P(\text{sea level})^{-z/H}$$

Thus, the microprocessor 810 recalls the absolute pressure value corresponding with the absolute pressure data and subtracts the barometric pressure value associated with the real-time barometric pressure data received 1630 from the remote microprocessor, to calculate gauge pressure 1640, which can be corrected for altitude based on the second equation. The final step is to display the gauge pressure 1650 on the interface 820 of the external monitor 800.

In an alternative embodiment (not shown) the gauge pressure calculation can be performed by an algorithm associated with the remote microprocessor rather than the microprocessor of the external monitor 800. In addition, the gauge pressure can be displayed 1650 on a monitor or other interface of an outside electronic device or computer. The electronic device or computer can either be coupled to the external monitor 800 through leads or connectors, or can otherwise communicate with the external monitor 800 through short-range telemetry, such as RF, microwave, acoustic, electromagnetic, light (e.g., infrared), etc.

Figure 20:
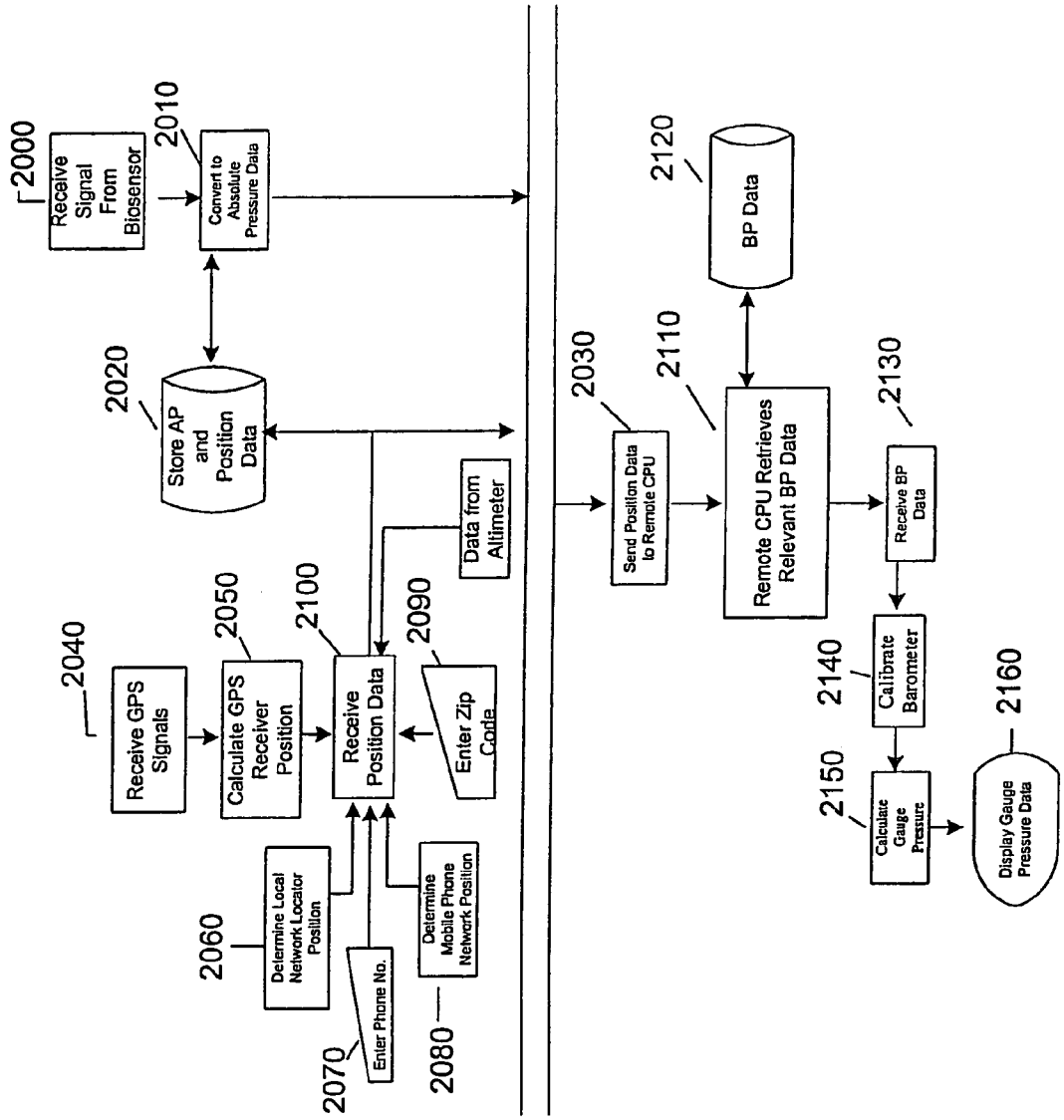
FIG. 20 is a flow chart of other embodiments of methods of the present invention.

FIG. 20 shows another embodiment of a method of correcting absolute pressure data received from an implantable biosensor, such as the biosensor 700 described above, to account for ambient (e.g., barometric) pressure. The method again utilizes an external monitor, such as the external monitor 800 described above, which is capable of performing the steps involved in the method. The method also utilizes a barometer 885. The barometer 885 can be integrated into the external monitor 800 and directly communicating with the microprocessor 810 of the external monitor 800. Alternatively, the barometer 885 can be a stand-alone device that is coupled to the external monitor 800 with leads or connectors or in communication with the external monitor 800 through short-range telemetry, such as RF, microwave, acoustic, electromagnetic, light (e.g., infrared), etc therewith.

The method includes the first step of using the external monitor 800 to receive a signal 2000 from a biosensor 700. The signal can be any telemetric signal such as acoustic, RF, electromagnetic, microwave, light (e.g., infrared) or any other form of telemetric signal. The signal can represent absolute pressure data. The next step can be to convert the signal into absolute pressure data 2010, which can be stored 2020 in a memory 830. This step can be accomplished with a transducer, such as the acoustic transducer 840 described above, for converting the telemetric signal into an electric signal, optical signal, or any other signal that can be transmitted to the microprocessor 810 of the external monitor 800. The microprocessor 810 can then process and store 2020 the absolute pressure data in a memory 830.

In parallel fashion, the external monitor 800 can receive position data 2100 from various sources. The position data can include altitude data as well. The position data is then used to obtain real-time barometric pressure data corresponding with the geographic location represented by the position data. The steps of obtaining the appropriate real-time barometric pressure data from a remote microprocessor are performed at steps 2030, 2110, 2120, and 2130. In one embodiment, the external monitor 800 includes a GPS receiver 860. The GPS receiver 860 can receive GPS signals 2040 from GPS satellites 920, and it can process geographic position data (including altitude data) 2050, thus determining the location of the external monitor 800 and consequently the biosensor 700, which is in close proximity to the external monitor 800. Alternatively, the geographic position of the external monitor 800 can be determined using a local network location system 2060. In yet another alternative embodiment, the position of the external monitor 800 can be determined by using a mobile telephone network location system 2080. Alternatively, the position of the external monitor 800 can be determined by entering a phone number 2070 or a zip code 2090 into an interface 820 keypad located on the external monitor 800. The microprocessor 810 of the external monitor 800 can either process the appropriate position data associated with the phone number or zip code by searching an internal database of phone numbers and/or zip codes with corresponding geographic position data. Alternatively, upon receiving position data 2100, the microprocessor 810 can store it 2020 in a retrievable database or memory 830, or it can send the position data to a remote microprocessor 2030 for use in retrieving relevant barometric pressure data 2110. If the geographic position data represents a telephone number or zip code rather than geographic position data, the remote microprocessor 810 can search its own database of phone numbers and zip codes for corresponding geographic location data. Alternatively, it can search an online database of telephone numbers and zip codes for corresponding geographic position data. The geographic position data is used by the remote microprocessor to select barometric pressure data corresponding with the geographic location represented by the geographic position data. Thus, the remote microprocessor searches a database of real-time barometric pressure data 2120, retrieves the appropriate data 2110, and sends it 2130 to the microprocessor 810 of the external monitor 800, which consequently receives that data. The real-time barometric pressure data is then used to calibrate 2140 the barometer 885. The calibration can be performed manually or automatically. In the case of automated calibration, the real-time barometric pressure data can be transmitted to the barometer, where a calibration algorithm associated with the barometer 885 microprocessor performs the calibration.

In another embodiment (not shown), the microprocessor 810 of the external monitor 800 can save and recall the barometric pressure data received from the barometer 885 and can calibrate that data based on the real-time barometric pressure data received from the remote microprocessor at step 2130. Thus, the calibration is performed by the microprocessor of the external monitor 800 rather than the barometer.

In addition, in the same manner as described with respect to the embodiment shown in FIG. 19, the microprocessor 810 of the external monitor 800 can include an algorithm 870 for calculating gauge pressure from absolute pressure using barometric pressure. The calculation involves subtracting the barometric pressure value from the absolute pressure value. Thus, the microprocessor 810 recalls the absolute pressure value corresponding with the absolute pressure data and subtracts the barometric pressure value obtained by the calibrated barometer 885, to calculate gauge pressure 2150. The final step is to display the gauge pressure 2160 on the interface 820 display on the external monitor 800 or the barometer 885.

In an alternative embodiment (not shown) the gauge pressure calculation can be performed by an algorithm associated with the remote microprocessor rather than the microprocessor 810 of the external monitor 800. In addition, the gauge pressure can be displayed 2160 on a monitor or other interface of an outside electronic device or computer. The electronic device or computer can either be coupled to the external monitor 800 through leads or connectors, or can otherwise communicate with the external monitor 800 through short-range telemetry, such as RF, microwave, acoustic, electromagnetic, light (e.g., infrared), etc.

Figure 21:
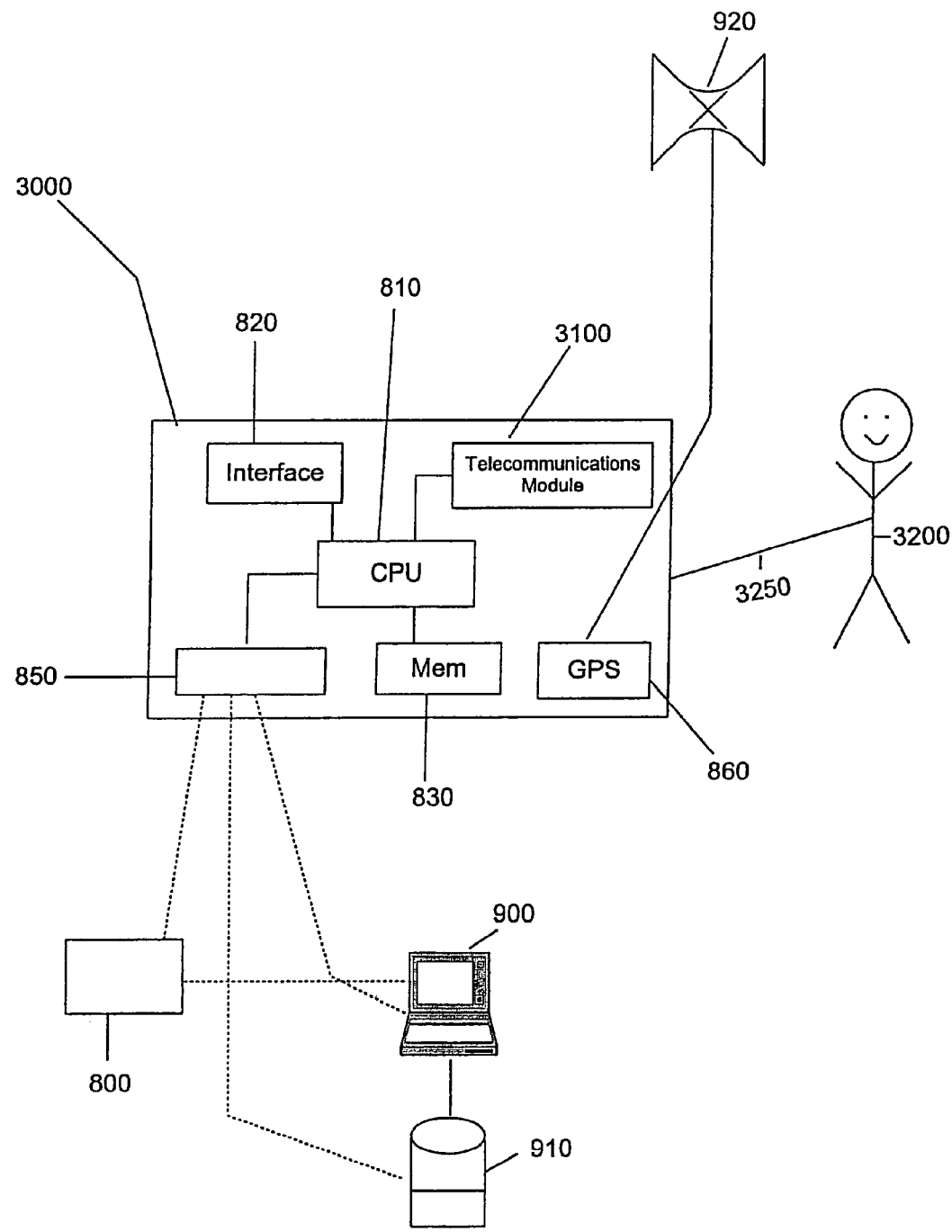
FIG. 21 is a diagram of a system for delivering barometric pressure information to a medical device.

As shown in FIG. 21, in which like numbers have been used to show like components with respect to the previous figures, the present systems and methods can also be used to provide barometric pressure information to any medical apparatus such as pacemakers, ventricular assist blood pumps, implantable and external drug delivery pumps such as insulin pumps, infusion pumps, artificial hearts, lung machines, drug infusion and drug release devices activated with telemetric signals, defibrillators, neurostimulating devices, aortic assistant balloons, intra ocular shunts for controlling intra ocular pressure, intra cranial shunts, incontinence control devices, contrast media automatic injectors, impotence devices, etc. A medical device 3000 is shown, which is modified to communicate with the external monitor 800, a computer system 900 or a remote source 910. The medical device 3000, for example an external insulin pump, which delivers insulin to the patient through an infusion set 3250 inserted under the skin of the patient. The device 3000 can include an interface 820, a micrprocessor 810 for controlling the pump, a GPS receiver 860 to communicate with a GPS satellite system 920 for determining the location of the pump, a memory 830, and antenna 850 for wireless communication with outside and/or remote sources. The device 3000 can include built in telecommunications hardware and software in a telecommunications module 3100 for communicating with a computer system 900 or a remote source of information 910, such as a web site. The computer system 900 or the remote source 910 can include real-time barometric pressure information for a plurality of geographic locations. Alternatively, the device 3000 can communicate with an external monitor 800, which can relay information from a computer system 900 or a remote source 910 to the device 3000.

It will be appreciated that the above descriptions are intended only to serve as examples, and that many other embodiments are possible within the spirit and the scope of the present invention.

What is claimed is:

1. A system for measuring pressure in a patient's body, comprising:
    an implant device configured for measuring absolute pressure in a body, the implant device further configured to communicate measured absolute pressure information outside of the body using telemetric signals; and
    an external monitor configured to
        receive telemetric signals from the implant device,
        receive barometric pressure information from a remote source, the barometric pressure information associated with a geographic location of the body, and
        derive gauge pressure from the received absolute pressure information and barometric pressure information, factoring in a correction factor based on the actual altitude of the implant device at the geographic location.

2. The system of claim 1, wherein the remote source comprises real-time barometric pressure information for a plurality of geographic locations.

3. The system of claim 1, further comprising a global positioning system (GPS) signal receiver coupled to at least one of the external monitor and the implant device.

4. The system of claim 3, wherein the external monitor is configured to receive position information from the GPS signal receiver and communicate the position information to the remote source, and wherein the received barometric pressure information corresponds to the position information.

5. A system for measuring pressure in a patient's body, comprising:
    an implant device configured for measuring absolute pressure in a body, the implant device further configured to communicate measured absolute pressure information outside of the body using telemetric signals; and
    an external monitor configured to
        receive telemetric signals comprising absolute pressure information from the implant device,
        transmit received absolute pressure information to a remote source, the remote source comprising real-time barometric pressure information corresponding with a geographic location of the body, and
        receive gauge pressure information from the remote source, the gauge pressure information derived from the absolute pressure information and barometric pressure information, factoring in a correction factor based on the actual altitude of the implant device at the geographic location.

6. The system of claim 5, wherein the remote source comprises real-time barometric pressure information for a plurality of geographic locations.

7. A system for measuring pressure in a patient's body, comprising:
    an external monitor configured to receive barometric pressure information from a remote source, the barometric pressure information associated with a geographic location of the body; and
    an implant device configured to
        receive barometric pressure information from the external monitor via acoustic telemetric signals,
        measure absolute pressure in a body, and
        derive gauge pressure from the received absolute pressure information and measured barometric pressure information, factoring in a correction factor based on the actual altitude of the implant device at the geographic location.

8. The system of claim 7, wherein the remote source comprises real time barometric pressure information for a plurality of geographic locations.

9. A method for measuring pressure in a patient's body, comprising:
    receiving a telemetric signal from a biosensor implanted in a body, the telemetric signal representing absolute pressure information;
    receiving real-time barometric pressure information from a remote source, the real-time barometric pressure information corresponding to a geographic location of the body; and
    deriving gauge pressure from the absolute pressure information and barometric pressure information, factoring in a correction factor based on the actual altitude of the biosensor at the geographic location.

10. The method of claim 9, wherein the geographic location of the body is determined using a GPS receiver.

11. The method of claim 9, wherein the geographic location of the body is determined based on a postal code.

12. The method of claim 9, wherein the geographic location of the body is determined based on a telephone number.

13. The method of claim 9, wherein the gauge pressure is derived by an external monitor proximate the body.

14. The method of claim 9, wherein the gauge pressure is derived by the implanted biosensor.

15. The method of claim 9, wherein the gauge pressure is derived by the remote source.

16. The method of claim 9, wherein the remote source comprises a web site comprising weather information.

17. The method of claim 9, further comprising displaying the gauge pressure value on a display proximate the body.

18. A method for measuring pressure in a patient's body, comprising:
receiving an acoustic signal from a biosensor implanted in a body;
deriving absolute pressure information from the acoustic signal;
receiving real-time barometric pressure information associated with a geographic location of the biosensor from a remote source; and
correcting the real-time barometric pressure information to factor in a correction factor based on the actual altitude of the bio sensor at the geographic location.

19. The method of claim 18, further comprising
calibrating a barometer according to the real-time barometric pressure information, factoring in the altitude of the bio sensor, the barometer in communication with an external monitor proximate the body;
using the calibrated barometer to determine an ambient pressure; and
deriving a gauge pressure based on the ambient pressure and absolute pressure information.

20. A system for measuring pressure in a patient's body, comprising;
an implant device for measuring intra-body absolute pressure, the implant device comprising
a pressure sensor, and
a transducer coupled to the pressure sensor for acquiring absolute pressure information from the pressure sensor, the transducer configured to transmit acoustic signals comprising absolute pressure information acquired from the pressure sensor;
an external monitor configured to receive acoustic signals from the implant device and to receive real-time barometric pressure information from a remote source, the remote source comprising real-time barometric pressure information for more than one geographic location; and
a global positioning system (GPS) signal receiver coupled to the external monitor,
the external monitor further configured to derive gauge pressure based on absolute pressure information received from the implant device and real-time barometric pressure received from the remote source, factoring in a correction factor based on the actual altitude of the implant device.

21. The system of claim 20, wherein the remote source comprises a web site comprising weather information.

22. A method for measuring pressure in a patient's body, comprising:
receiving an acoustic signal from a biosensor implanted in the body;
deriving absolute pressure information from the acoustic signal;
establishing a communications link with a remote source comprising real-time barometric pressure information for more than one geographic location;
through the communications link, receiving real-time barometric pressure information from the remote source;
deriving gauge pressure by subtracting a pressure value corresponding with the real-time barometric pressure information from a pressure value corresponding with the absolute pressure information, and factoring in a correction factor based on the actual altitude of the bio sensor; and
displaying said gauge pressure on a display.

23. The method of claim 22, further comprising determining a geographic location and altitude of the bio sensor using a GPS receiver, wherein the real-time barometric pressure information from the remote source corresponds with the geographic location determined by the GPS receiver.

24. The method of claim 22, wherein the remote source is associated with a web site comprising weather information.

25. A method for communicating with a device implanted in a patient's body, comprising:
receiving an acoustic telemetric signal from the device, the acoustic telemetric signal representing absolute pressure information;
receiving real-time barometric pressure information from a remote source, the real-time barometric pressure information corresponding to a geographic location of the body; and
deriving gauge pressure from the absolute pressure information and barometric pressure information, factoring in a correction factor based on the actual altitude of the device.

26. The method of claim 25, wherein the device is a biosensor.

27. The method of claim 25, wherein the device is a drug infusion pump.

28. The method of claim 25, wherein the remote source comprises a web site comprising weather information.

29. A method for providing barometric pressure information to a medical device comprising:
determining the geographic location of the medical device;
receiving real-time barometric pressure information from a remote source, said remote source comprising real-time barometric pressure information for a plurality of geographic locations, the real-time barometric pressure information corresponding to a geographic location of the medical device;
correcting the real-time barometric pressure information to factor in a correction factor based on the actual altitude of the medical device; and
transmitting an acoustic signal to the medical device, the acoustic signal comprising the corrected real-time barometric pressure information.

30. The system of claim 1, the monitor further comprising a device for determining the altitude of the implant device at the geographic location.

31. The system of claim 30, wherein the device for determining the altitude of the implant device comprises at least one of an altimeter and a global positioning system (GPS) receiver.

32. A system for measuring pressure in a patient's body, comprising:
an implant device configured for measuring absolute pressure in a body, the implant device further configured to communicate measured absolute pressure information outside of the body using telemetric signals; and
an external monitor configured to
receive telemetric signals from the implant device,
receive barometric pressure information from a remote source, the barometric pressure information associated with a geographic location of the body, and derive gauge pressure from the received absolute pressure information and barometric pressure information, factoring in altitude of the implant device at the geographic location, the monitor further comprising a device for determining the altitude of the implant device at the geographic location, and the external monitor configured for correcting the barometric pressure information from the remote source based upon the altitude of the implant device using an equation: $P(z) = P \text{ (sea level)}^{-z/H}$, where z=height in meters corresponding to the altitude of the implant device and H=scale height.

* * * * *

UNITED STATES PATENT AND TRADEMARK OFFICE
CERTIFICATE OF CORRECTION

PATENT NO. : 7,273,457 B2
APPLICATION NO. : 10/152091
DATED : September 25, 2007
INVENTOR(S) : Avi Penner It is certified that error appears in the above-identified patent and that said Letters Patent is hereby corrected as shown below:

Column 9, line 44
Delete "5100" and replace it with -- 5-100 --

Column 13, line 53
Delete "0.52.5" and replace it with -- 0.5-2.5 --

Column 14, line 16
Delete "carbonfluorine" and replace it with -- carbon-flourine --

Column 17, line 38
Delete "fieldeffect" and replace it with -- field-effect --

Column 21, line 11
Delete "drift The casing" and replace it with -- drift. The casing --

Column 28, line 29
Delete "P(sea level)=seal level" and replace it with -- P(sea level)=sea level --

Column 30, line 31
Delete "interface 826" and replace it with -- interface 820 --

Column 32, line 67
Delete "p ressure" and replace it with -- pressure --

Column 37, line 12
Delete "bio sensor" and replace it with -- biosensor --

Column 37, line 16
Delete "bio sensor" and replace it with -- biosensor --

UNITED STATES PATENT AND TRADEMARK OFFICE
CERTIFICATE OF CORRECTION

PATENT NO. : 7,273,457 B2
APPLICATION NO. : 10/152091
DATED : September 25, 2007
INVENTOR(S) : Avi Penner It is certified that error appears in the above-identified patent and that said Letters Patent is hereby corrected as shown below:

Column 37, lines 65-66
Delete "bio sensor" and replace it with -- biosensor --

Column 38, line 2
Delete "bio sensor" and replace it with -- biosensor --

Signed and Sealed this

Twenty-ninth Day of April, 2008

JON W. DUDAS
*Director of the United States Patent and Trademark Office*